US008343735B2

(12) United States Patent
Van Kimmenade et al.

(10) Patent No.: US 8,343,735 B2
(45) Date of Patent: Jan. 1, 2013

(54) MODIFIED SECRETION SYSTEM TO INCREASE EXPRESSION OF POLYPEPTIDES IN BACTERIA

(75) Inventors: Anita Van Kimmenade, San Bruno, CA (US); Carol Fioresi, Redwood City, CA (US); Caroline Peres, Palo Alto, CA (US); Eugenio Ferrari, San Bruno, CA (US)

(73) Assignee: Danisco US Inc., Palo Alto, CA (US)

( * ) Notice: Subject to any disclaimer, the term of this patent is extended or adjusted under 35 U.S.C. 154(b) by 328 days.

(21) Appl. No.: 12/598,182

(22) PCT Filed: May 12, 2008

(86) PCT No.: PCT/US2008/063418

§ 371 (c)(1),
(2), (4) Date: Mar. 25, 2010

(87) PCT Pub. No.: WO2008/141281

PCT Pub. Date: Nov. 20, 2008

(65) Prior Publication Data

US 2010/0184137 A1    Jul. 22, 2010

Related U.S. Application Data

(60) Provisional application No. 60/928,875, filed on May 10, 2007.

(51) Int. Cl.
*C12P 21/06* (2006.01)
*C12N 9/52* (2006.01)
*C12N 1/20* (2006.01)
*C12N 15/63* (2006.01)

(52) U.S. Cl. ............. 435/69.1; 435/221; 435/252.31; 435/320.1; 536/23.2

(58) Field of Classification Search .................. None
See application file for complete search history.

(56) References Cited

U.S. PATENT DOCUMENTS

| | | | |
|---|---|---|---|
| 4,302,544 A | 11/1981 | Young et al. |
| 4,450,235 A | 5/1984 | Dean et al. |
| 4,914,031 A | 4/1990 | Zukowski et al. |
| 4,980,288 A | 12/1990 | Bryan et al. |
| 5,208,158 A | 5/1993 | Bech et al. |
| 5,217,878 A | 6/1993 | van Eekelen et al. |
| RE34,606 E | 5/1994 | Estell et al. |
| 5,310,675 A | 5/1994 | Estell et al. |
| 5,336,611 A | 8/1994 | van Eekelen et al. |
| 5,399,283 A | 3/1995 | Stabinsky et al. |
| 5,441,882 A | 8/1995 | Estell et al. |
| 5,482,849 A | 1/1996 | Branner et al. |
| 5,631,217 A | 5/1997 | Branner et al. |
| 5,665,587 A | 9/1997 | Aaslyng et al. |
| 5,700,676 A | 12/1997 | Bott et al. |
| 5,741,694 A | 4/1998 | Hastrup et al. |
| 5,858,757 A | 1/1999 | Von Der Osten et al. |
| 5,880,080 A | 3/1999 | Amory et al. |
| 6,197,567 B1 | 3/2001 | Aaslyng et al. |
| 6,218,165 B1 | 4/2001 | Estell et al. |
| 6,376,450 B1 | 4/2002 | Ghosh et al. |
| 6,911,322 B2 | 6/2005 | Valle et al. |

FOREIGN PATENT DOCUMENTS

| | | |
|---|---|---|
| EP | 0 134 048 A1 | 3/1985 |
| WO | WO 89/06279 A1 | 7/1989 |
| WO | WO 99/20726 A1 | 4/1999 |
| WO | WO 99/20769 A2 | 4/1999 |
| WO | WO 99/20770 A2 | 4/1999 |
| WO | WO 99/34011 A2 | 7/1999 |
| WO | WO 2004/060909 A2 | 7/2004 |

OTHER PUBLICATIONS

Altschul, S.F. et al. "Local alignment statistics." *Methods Enzymol* 266:460-80, 1996.
Altschul, S.F. et al. "Basic local alignment search tool." *J. Mol. Biol* 215(3):403-410, 1990.
Aunstrup, K. et al. "Proteases from alkalophilic *Bacillus* species." *Proc. IV IFS: Ferment. Technol. Today*:299-305, 1972.
Bost, S. et al. "prl Mutations in the *Escherichia coli* secG Gene." *Journal of Biological Chemistry* 272(7):4087-4093, 1997.
Bost, S. et al. "Both transmembrane domains of SecG contribute to signal sequence recognition by the *Escherichia coli* protein export machinery." *Molecular Microbiology* 38(3):575-587, 2000.
DelMar, E.G. et al. "A sensitive new substrate for chymotrypsin." *Analytical Biochemistry* 99(2):316-320, 1979.
Devereux, P. et al. "A comprehensive set of sequence analysis programs for the VAX." *Nucl. Acids Res* 12:387-395, 1984.
Estell, D.A. et al. "Engineering an enzyme by site-directed mutagenesis to be resistant to chemical oxidation." *J. Biol. Chem.* 260(11):6518-6521, 1985.
Fahnestock, S.R. et al. "Expression of the staphylococcal protein A gene in *Bacillus subtilis* by gene fusions utilizing the promoter from a *Bacillus* amyloliquefaciens alpha-amylase gene." *J. Bacteriol.* 165(3):796-804, 1986.
Feng, D.F. et al. "Progressive sequence alignment as a prerequisite to correct phylogenetic trees." *J. Mol. Evol* 25(4):351-360, 1987.
Higgins, D.G. et al. "Fast and sensitive multiple alignment sequence on a microcomputer." *CABIOS* 5:151-153, 1989.
Hoch, J.A. et al. "Chromosomal location of pleiotropic negative sporulation mutations in *Bacillus subtilis*." *Genetics* 73(2):215-28, 1973.
Kalisz, H.M. "Microbial proteinases." *Advances in Biochemical Engineering/Biotechnology* 36:1-65, 1988.
Karlin, S. et al. "Applications and statistics for multiple high-scoring segments in molecular sequences." *Proc. Natl. Acad. Sci. USA* 90(12):5873-7, 1993.
Van der Laan, J.C. et al. "Cloning, characterization, and multiple chromosomal integration of a *Bacillus* alkaline protease gene." *Appl. Environ. Microbiol.* 57(4):901-909, 1991.

(Continued)

*Primary Examiner* — Kagnew H Gebreyesus
(74) *Attorney, Agent, or Firm* — Danisco US Inc.

(57) ABSTRACT

The present invention provides methods of altering the production of desired polypeptides in a host cell. In particular, the present invention provides polynucleotides encoding truncated SecG proteins capable of facilitating the secretion of desired proteases by a bacterial host cell, such as *Bacillus* species, as well as expression vectors and a host cell containing the polynucleotides.

21 Claims, 9 Drawing Sheets

OTHER PUBLICATIONS

Needleman, S.B. et al. "A general method applicable to the search for similarities in the amino acid sequence of two proteins." *J. Mol. Biol* 48(3):443-53, 1970.

Palva, I. "Molecular cloning of alpha-amylase gene from *Bacillus amyloliquefaciens* and its expression in *B. subtilis*." *Gene* 19(1):81-7, 1982.

Pearson, W.R. et al. "Improved Tools for Biological Sequence Comparison." *Proc. Natl. Acad. Sci. USA* 85(8):2444-2448, 1988.

Power, S.D. et al. "Secretion and autoproteolytic maturation of subtilisin." *Proc. Natl. Acad. Sci. U.S.A* 83(10):3096-100, 1986.

Satoh, Y. et al. "Nearest Neighbor Analysis of the SecYEG Complex. 1. Identification of a SecY-SecG Interface†." *Biochemistry* 42(24):7434-7441, 2003.

Smith, T.F. et al. "Comparison of biosequences." *Adv. Appl. Math* 2:482-489, 1981.

Stahl, M.L. et al. "Replacement of the *Bacillus subtilis* subtilisin structural gene with an in vitro-derived deletion mutation.." *J. Bacteriol.* 158(2):411-418, 1984.

Swaving, J. et al. "Preprotein Translocation by a Hybrid Translocase Composed of *Escherichia coli* and *Bacillus subtilis* Subunits." *J. Bacteriol.* 181(22):7021-7027, 1999.

Wang, L. et al. "Engineering the Independent Folding of the Subtilisin BPN' Pro-Domain: Correlation of Pro-Domain Stability with the Rate of Subtilisin Folding." *Biochemistry* 37(9):3165-3171, 1998.

Wang, L.F. et al. "Expression and secretion of human atrial natriuretic alpha-factor in *Bacillus subtilis* using the subtilisin signal peptide." *Gene* 69(1):39-47, 1988.

SEQUENCE LISTING

<160> NUMBER OF SEQ ID NOS: 41

<210> SEQ ID NO 1
<211> LENGTH: 78
<212> TYPE: PRT
<213> ORGANISM: Geobacillus thermodenitrificans

<400> SEQUENCE: 1

Met His Ala Leu Leu Val Thr Leu Leu Val Ile Val Ser Ile Ala Leu
1               5                   10                  15

Ile Ala Ile Val Leu Leu Gln Ser Gly Arg Ser Ala Gly Leu Ser Gly
                20                  25                  30

Ala Ile Thr Gly Gly Ala Glu Gln Leu Phe Gly Lys Gln Lys Ala Arg
            35                  40                  45

-continued

Gly Leu Asp Ala Val Phe Gln Arg Val Thr Val Leu Ala Ile Leu
    50                  55                  60

Tyr Phe Val Leu Thr Ile Leu Val Ala Tyr Val Gln Pro Ser
 65                  70                  75

<210> SEQ ID NO 2
<211> LENGTH: 77
<212> TYPE: PRT
<213> ORGANISM: Listeria welshimeri serovar

<400> SEQUENCE: 2

Met Ser Thr Val Leu Thr Val Leu Leu Ile Ile Val Ser Val Leu Leu
 1               5                  10                  15

Ile Thr Val Ile Ile Leu Gln Pro Gly Lys Ser Ala Gly Leu Ser Gly
                20                  25                  30

Ala Ile Ser Gly Gly Ala Glu Gln Leu Phe Gly Lys Gln Lys Ala Arg
            35                  40                  45

Gly Leu Glu Leu Ile Leu His Arg Thr Thr Ile Val Leu Ser Val Val
    50                  55                  60

Phe Phe Val Ile Leu Ile Ala Leu Ala Tyr Phe Val Gln
 65                  70                  75

<210> SEQ ID NO 3
<211> LENGTH: 76
<212> TYPE: PRT
<213> ORGANISM: Bacillus licheniformis

<400> SEQUENCE: 3

Met Ala Ala Phe Leu Thr Val Leu Leu Val Ile Val Ser Ile Val Leu
 1               5                  10                  15

Ile Val Val Val Leu Leu Gln Ser Gly Lys Ser Ala Gly Leu Ser Gly
                20                  25                  30

Ala Ile Ser Gly Gly Ala Glu Gln Leu Phe Gly Lys Gln Lys Ala Arg
            35                  40                  45

Gly Leu Asp Leu Ile Leu His Arg Met Thr Val Val Leu Thr Val Leu
    50                  55                  60

Phe Phe Phe Leu Thr Ile Ala Leu Ala Tyr Phe Val
 65                  70                  75

<210> SEQ ID NO 4
<211> LENGTH: 76
<212> TYPE: PRT
<213> ORGANISM: Bacillus subtilis

<400> SEQUENCE: 4

Met His Ala Val Leu Ile Thr Leu Leu Val Ile Val Ser Ile Ala Leu
 1               5                  10                  15

Ile Ile Val Val Leu Leu Gln Ser Ser Lys Ser Ala Gly Leu Ser Gly
                20                  25                  30

Ala Ile Ser Gly Gly Ala Glu Gln Leu Phe Gly Lys Gln Lys Ala Arg
            35                  40                  45

Gly Leu Asp Leu Ile Leu His Arg Ile Thr Val Leu Ala Val Leu
    50                  55                  60

Phe Phe Val Leu Thr Ile Ala Leu Ala Tyr Ile Leu
 65                  70                  75

<210> SEQ ID NO 5
<211> LENGTH: 78
<212> TYPE: PRT
<213> ORGANISM: Lactobacillus plantarum

```
<400> SEQUENCE: 5

Met Tyr Asn Leu Leu Thr Leu Ile Leu Val Ser Val Leu Ile
1               5                   10                  15

Ile Ile Ala Val Met Met Gln Pro Ser Lys Thr Asn Asp Ala Met Ser
            20                  25                  30

Ser Leu Thr Gly Gly Ala Asp Asp Leu Phe Ala Lys Gln Lys Pro Arg
        35                  40                  45

Gly Phe Glu Ala Phe Met Gln Lys Val Thr Val Leu Gly Ile Ala
    50                  55                  60

Phe Phe Ile Leu Ala Leu Ala Leu Ala Trp Tyr Ser Ser Lys
65                  70                      75

<210> SEQ ID NO 6
<211> LENGTH: 78
<212> TYPE: PRT
<213> ORGANISM: Lactobacillus casei

<400> SEQUENCE: 6

Met Gln Ser Leu Leu Thr Thr Phe Leu Val Ile Asp Ser Ile Leu Ile
1               5                   10                  15

Val Ile Ala Thr Leu Met Gln Pro Ser Lys Gln Gln Asp Ala Leu Ser
            20                  25                  30

Ala Leu Ser Gly Gly Ala Thr Asp Leu Phe Gly Lys Thr Lys Ser Arg
        35                  40                  45

Gly Phe Glu Ala Phe Met Glu Lys Val Thr Val Ala Leu Gly Val Ile
    50                  55                  60

Phe Phe Gly Leu Ala Ile Ala Leu Val Tyr Leu Glu Ala His
65                  70                      75

<210> SEQ ID NO 7
<211> LENGTH: 77
<212> TYPE: PRT
<213> ORGANISM: Staphylococcus aureus

<400> SEQUENCE: 7

Met His Thr Phe Leu Ile Val Leu Leu Ile Ile Asp Cys Ile Ala Leu
1               5                   10                  15

Ile Thr Val Val Leu Leu Gln Glu Gly Lys Ser Ser Gly Phe Ser Gly
            20                  25                  30

Ala Ile Ser Gly Gly Ala Glu Gln Leu Phe Gly Lys Gln Lys Gln Arg
        35                  40                  45

Gly Val Asp Leu Phe Leu Asn Arg Leu Thr Ile Ile Leu Ser Ile Leu
    50                  55                  60

Phe Phe Val Leu Met Ile Cys Ile Ser Tyr Leu Gly Met
65                  70                      75

<210> SEQ ID NO 8
<211> LENGTH: 110
<212> TYPE: PRT
<213> ORGANISM: Escherichia coli

<400> SEQUENCE: 8

Met Tyr Glu Ala Leu Leu Val Val Phe Leu Ile Val Ala Ile Gly Leu
1               5                   10                  15

Val Gly Leu Ile Met Leu Gln Gln Gly Lys Gly Ala Asp Met Gly Ala
            20                  25                  30

Ser Phe Gly Ala Gly Ala Ser Ala Thr Leu Phe Gly Ser Ser Gly Ser
        35                  40                  45
```

```
Gly Asn Phe Met Thr Arg Met Thr Ala Leu Leu Ala Thr Leu Phe Phe
    50                  55                  60

Ile Ile Ser Leu Val Leu Gly Asn Ile Asn Ser Asn Lys Thr Asn Lys
65                  70                  75                  80

Gly Ser Glu Trp Glu Asn Leu Ser Ala Pro Ala Lys Thr Glu Gln Thr
                85                  90                  95

Gln Pro Ala Ala Pro Ala Lys Pro Thr Ser Asp Ile Pro Asn
            100                 105                 110

<210> SEQ ID NO 9
<211> LENGTH: 76
<212> TYPE: PRT
<213> ORGANISM: Bacillus clausii

<400> SEQUENCE: 9

Met Gln Leu Phe Leu Met Ile Ala Leu Ile Ile Val Ser Val Leu Leu
1               5                   10                  15

Val Ala Val Val Leu Leu Gln Pro Gly Arg Ser Ser Gly Leu Ser Gly
                20                  25                  30

Ala Ile Thr Gly Gly Ala Glu Gln Leu Gly Lys Gln Lys Ala Arg
        35                  40                  45

Gly Leu Asp Ala Val Leu His Arg Ala Thr Ile Val Leu Ala Val Leu
    50                  55                  60

Phe Phe Ile Leu Thr Gly Leu Asn Ala Tyr Phe Leu
65                  70                  75

<210> SEQ ID NO 10
<211> LENGTH: 231
<212> TYPE: DNA
<213> ORGANISM: Bacillus clausii

<400> SEQUENCE: 10
atgcagctgt ttttgatgat cgcattaatt attgtttctg tcctcttagt cgctgtcgtt      60
cttttgcagc caggtcgcag ctctgggtta tcgggcgcca ttactggagg ggcagagcag     120
ttgctaggaa acaaaaagc gcgcgggctt gatgcgtat gcatcgagc aacaatcgta       180 cttgctgttt tgttttttat tttgacaggg ttaaatgcgt atttcctata a              231

<210> SEQ ID NO 11
<211> LENGTH: 39
<212> TYPE: PRT
<213> ORGANISM: Bacillus clausii

<400> SEQUENCE: 11

Met Gln Leu Phe Leu Met Ile Ala Leu Ile Ile Val Ser Val Leu Leu
1               5                   10                  15

Val Ala Val Val Leu Leu Gln Pro Gly Arg Ser Ser Gly Leu Ser Gly
                20                  25                  30

Ala Ile Thr Gly Gly Ala Glu
        35

<210> SEQ ID NO 12
<211> LENGTH: 231
<212> TYPE: DNA
<213> ORGANISM: Artificial
<220> FEATURE:
<223> OTHER INFORMATION: synthetic mutated Bacillus clausii sequence

<400> SEQUENCE: 12
atgcagctgt ttttgatgat cgcattaatt attgtttctg tcctcttagt cgctgtcgtt      60
```

```
cttttgcagc caggtcgcag ctctgggtta tcgggcgcca ttactggagg ggcagagtag    120
ttgctaggaa aacaaaaagc gcgcgggctt gatgcggtat tgcatcgagc aacaatcgta    180
cttgctgttt tgttttttat tttgacaggg ttaaatgcgt atttcctata a             231
```

<210> SEQ ID NO 13
<211> LENGTH: 37
<212> TYPE: DNA
<213> ORGANISM: Artificial
<220> FEATURE:
<223> OTHER INFORMATION: synthetic primer

<400> SEQUENCE: 13

```
ggcgcgcccg gggaggatct ttttactat gatttcg                              37
```

<210> SEQ ID NO 14
<211> LENGTH: 44
<212> TYPE: DNA
<213> ORGANISM: Artificial
<220> FEATURE:
<223> OTHER INFORMATION: synthetic primer

<400> SEQUENCE: 14

```
tgcgatcatc aaaaacagct gcatcccata cacctccaga ctca                     44
```

<210> SEQ ID NO 15
<211> LENGTH: 43
<212> TYPE: DNA
<213> ORGANISM: Artificial
<220> FEATURE:
<223> OTHER INFORMATION: synthetic primer

<400> SEQUENCE: 15

```
gggttaaatg cgtatttcct ataaggcggc aatgtttgta taa                      43
```

<210> SEQ ID NO 16
<211> LENGTH: 35
<212> TYPE: DNA
<213> ORGANISM: Artificial
<220> FEATURE:
<223> OTHER INFORMATION: synthetic primer

<400> SEQUENCE: 16

```
gcgcggagct cgcttccgta atatttaaca tctcc                               35
```

<210> SEQ ID NO 17
<211> LENGTH: 44
<212> TYPE: DNA
<213> ORGANISM: Artificial
<220> FEATURE:
<223> OTHER INFORMATION: synthetic primer

<400> SEQUENCE: 17

```
tgagtctgga ggtgtatggg atgcagctgt ttttgatgat cgca                     44
```

<210> SEQ ID NO 18
<211> LENGTH: 43
<212> TYPE: DNA
<213> ORGANISM: Artificial
<220> FEATURE:
<223> OTHER INFORMATION: synthetic primer

<400> SEQUENCE: 18

```
ttatacaaac attgccgcct tataggaaat acgcatttaa ccc                      43
```

```
<210> SEQ ID NO 19
<211> LENGTH: 50
<212> TYPE: DNA
<213> ORGANISM: Artificial
<220> FEATURE:
<223> OTHER INFORMATION: synthetic primer

<400> SEQUENCE: 19
ggatccagct tatcgatacc gtcgattata ggaaatacgc atttaaccct          50

<210> SEQ ID NO 20
<211> LENGTH: 50
<212> TYPE: DNA
<213> ORGANISM: Artificial
<220> FEATURE:
<223> OTHER INFORMATION: synthetic primer

<400> SEQUENCE: 20
agggttaaat gcgtatttcc tataatcgac ggtatcgata agctggatcc          50

<210> SEQ ID NO 21
<211> LENGTH: 50
<212> TYPE: DNA
<213> ORGANISM: Artificial
<220> FEATURE:
<223> OTHER INFORMATION: synthetic primer

<400> SEQUENCE: 21
catcagacct tatacaaaca ttgccggcct aggatgcata tggcggccgc          50

<210> SEQ ID NO 22
<211> LENGTH: 50
<212> TYPE: DNA
<213> ORGANISM: Artificial
<220> FEATURE:
<223> OTHER INFORMATION: synthetic primer

<400> SEQUENCE: 22
gcggccgcca tatgcatcct aggccggcaa tgtttgtata aggtctgatg          50

<210> SEQ ID NO 23
<211> LENGTH: 41
<212> TYPE: DNA
<213> ORGANISM: Artificial
<220> FEATURE:
<223> OTHER INFORMATION: synthetic primer

<400> SEQUENCE: 23
cagcttatcg ataccgtcga cccatacacc tccagactca c                    41

<210> SEQ ID NO 24
<211> LENGTH: 41
<212> TYPE: DNA
<213> ORGANISM: Artificial
<220> FEATURE:
<223> OTHER INFORMATION: synthetic primer

<400> SEQUENCE: 24
gtgagtctgg aggtgtatgg gtcgacggta tcgataagct g                    41

<210> SEQ ID NO 25
<211> LENGTH: 380
<212> TYPE: PRT
<213> ORGANISM: Bacillus alcalophilus

<400> SEQUENCE: 25

Met Lys Lys Pro Leu Gly Lys Ile Val Ala Ser Thr Ala Leu Leu Ile
```

```
            1               5                  10                 15
Ser Val Ala Phe Ser Ser Ile Ala Ser Ala Glu Glu Ala Lys
             20                 25                 30

Glu Lys Tyr Leu Ile Gly Phe Asn Glu Gln Glu Ala Val Ser Glu Phe
             35                 40                 45

Val Glu Gln Val Glu Ala Asn Asp Glu Val Ala Ile Leu Ser Glu Glu
             50                 55                 60

Glu Val Glu Ile Glu Leu Leu His Glu Phe Glu Thr Ile Pro Val
 65                 70                 75                 80

Leu Ser Val Glu Leu Ser Pro Glu Asp Val Asp Ala Leu Glu Leu Asp
                 85                 90                 95

Pro Ala Ile Ser Tyr Ile Glu Glu Asp Ala Glu Val Thr Thr Met Ala
                100                105                110

Gln Ser Val Pro Trp Gly Ile Ser Arg Val Gln Ala Pro Ala Ala His
                115                120                125

Asn Arg Gly Leu Thr Gly Ser Gly Val Lys Val Ala Val Leu Asp Thr
                130                135                140

Gly Ile Ser Thr His Pro Asp Leu Asn Ile Arg Gly Gly Ala Ser Phe
145                150                155                160

Val Pro Gly Glu Pro Ser Thr Gln Asp Gly Asn Gly His Gly Thr His
                165                170                175

Val Ala Gly Thr Ile Ala Ala Leu Asn Asn Ser Ile Gly Val Leu Gly
                180                185                190

Val Ala Pro Asn Ala Glu Leu Tyr Ala Val Lys Val Leu Gly Ala Ser
                195                200                205

Gly Ser Gly Ser Val Ser Ser Ile Ala Gln Gly Leu Glu Trp Ala Gly
                210                215                220

Asn Asn Gly Met His Val Ala Asn Leu Ser Leu Gly Ser Pro Ser Pro
225                230                235                240

Ser Ala Thr Leu Glu Gln Ala Val Asn Ser Ala Thr Ser Arg Gly Val
                245                250                255

Leu Val Val Ala Ala Ser Gly Asn Ser Gly Ala Gly Ser Ile Ser Tyr
                260                265                270

Pro Ala Arg Tyr Ala Asn Ala Met Ala Val Gly Ala Thr Asp Gln Asn
                275                280                285

Asn Asn Arg Ala Ser Phe Ser Gln Tyr Gly Ala Gly Leu Asp Ile Val
                290                295                300

Ala Pro Gly Val Asn Val Gln Ser Thr Tyr Pro Gly Ser Thr Tyr Ala
305                310                315                320

Ser Leu Asn Gly Thr Ser Met Ala Thr Pro His Val Ala Gly Ala Ala
                325                330                335

Ala Leu Val Lys Gln Lys Asn Pro Ser Trp Ser Asn Val Gln Ile Arg
                340                345                350

Asn His Leu Lys Asn Thr Ala Thr Ser Leu Gly Ser Thr Asn Leu Tyr
                355                360                365

Gly Ser Gly Leu Val Asn Ala Glu Ala Ala Thr Arg
                370                375                380

<210> SEQ ID NO 26
<211> LENGTH: 380
<212> TYPE: PRT
<213> ORGANISM: Bacillus clausii

<400> SEQUENCE: 26

Val Arg Ser Lys Lys Leu Trp Ile Val Ala Ser Thr Ala Leu Leu Ile
```

```
1               5                   10                  15
Ser Val Ala Phe Ser Ser Ile Ala Ser Ala Glu Glu Ala Lys
                20                  25                  30
Glu Lys Tyr Leu Ile Gly Phe Asn Glu Gln Glu Ala Val Ser Glu Phe
            35                  40                  45
Val Glu Gln Val Glu Ala Asn Asp Glu Val Ala Ile Leu Ser Glu Glu
50                  55                  60
Glu Val Glu Ile Glu Leu Leu His Glu Phe Glu Thr Ile Pro Val
65                  70                  75                  80
Leu Ser Val Glu Leu Ser Pro Glu Asp Val Asp Ala Leu Glu Leu Asp
                85                  90                  95
Pro Ala Ile Ser Tyr Ile Glu Glu Asp Ala Glu Val Thr Thr Met Ala
                100                 105                 110
Gln Ser Val Pro Trp Gly Ile Ser Arg Val Gln Ala Pro Ala Ala His
            115                 120                 125
Asn Arg Gly Leu Thr Gly Ser Gly Val Lys Val Ala Val Leu Asp Thr
130                 135                 140
Gly Ile Ser Thr His Pro Asp Leu Asn Ile Arg Gly Gly Ala Ser Phe
145                 150                 155                 160
Val Pro Gly Glu Pro Ser Thr Gln Asp Gly Asn Gly His Gly Thr His
                165                 170                 175
Val Ala Gly Thr Ile Ala Ala Leu Asn Asn Ser Ile Gly Val Leu Gly
                180                 185                 190
Val Ala Pro Asn Ala Glu Leu Tyr Ala Val Lys Val Leu Gly Ala Ser
                195                 200                 205
Gly Ser Gly Ser Val Ser Ser Ile Ala Gln Gly Leu Glu Trp Ala Gly
            210                 215                 220
Asn Asn Val Met His Val Ala Asn Leu Ser Leu Gly Leu Gln Ala Pro
225                 230                 235                 240
Ser Ala Thr Leu Glu Gln Ala Val Asn Ser Ala Thr Ser Arg Gly Val
                245                 250                 255
Leu Val Val Ala Ala Ser Gly Asn Ser Gly Ala Gly Ser Ile Ser Tyr
                260                 265                 270
Pro Ala Arg Tyr Ala Asn Ala Met Ala Val Gly Ala Thr Asp Gln Asn
            275                 280                 285
Asn Asn Arg Ala Ser Phe Ser Gln Tyr Gly Ala Gly Leu Asp Ile Val
290                 295                 300
Ala Pro Gly Val Asn Val Gln Ser Thr Tyr Pro Gly Ser Thr Tyr Ala
305                 310                 315                 320
Ser Leu Asn Gly Thr Ser Met Ala Thr Pro His Val Ala Gly Ala Ala
                325                 330                 335
Ala Leu Val Lys Gln Lys Asn Pro Ser Trp Ser Asn Val Gln Ile Arg
                340                 345                 350
Asn His Leu Lys Asn Thr Ala Thr Ser Leu Gly Ser Thr Asn Leu Tyr
            355                 360                 365
Gly Ser Gly Leu Val Asn Ala Glu Ala Ala Thr Arg
370                 375                 380

<210> SEQ ID NO 27
<211> LENGTH: 380
<212> TYPE: PRT
<213> ORGANISM: Artificial
<220> FEATURE:
<223> OTHER INFORMATION: synthetic Bacillus variant

<400> SEQUENCE: 27
```

```
Val Arg Ser Lys Lys Leu Trp Ile Val Ala Ser Thr Ala Leu Leu Ile
1               5                   10                  15

Ser Val Ala Phe Ser Ser Ile Ala Ser Ala Glu Glu Ala Lys
            20              25                  30

Gln Lys Tyr Leu Ile Gly Phe Asn Glu Gln Glu Ala Val Ser Glu Phe
            35                  40                  45

Val Glu Gln Val Glu Ala Asn Asp Glu Val Ala Ile Leu Ser Glu Glu
50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110

Gln Ser Val Pro Trp Gly Ile Ser Arg Val Gln Ala Pro Ala Ala His
            115                 120                 125

Asn Arg Gly Leu Thr Gly Ser Gly Val Lys Val Ala Val Leu Asp Thr
130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
            165                 170                 175

Val Ala Gly Thr Ile Ala Ala Leu Asn Asn Ser Ile Gly Val Leu Gly
            180                 185                 190

Val Ala Pro Asn Ala Glu Leu Tyr Ala Val Lys Val Leu Gly Ala Ser
            195                 200                 205

Gly Ser Gly Ser Val Ser Ser Ile Ala Gln Gly Leu Glu Trp Ala Gly
            210                 215                 220

Asn Asn Val Met His Val Ala Asn Leu Ser Leu Gly Leu Gln Ala Pro
225                 230                 235                 240

Ser Ala Thr Leu Glu Gln Ala Val Asn Ser Ala Thr Ser Arg Gly Val
            245                 250                 255

Leu Val Val Ala Ala Ser Gly Asn Ser Gly Ala Gly Ser Ile Ser Tyr
            260                 265                 270

Pro Ala Arg Tyr Ala Asn Ala Met Ala Val Gly Ala Thr Asp Gln Asn
            275                 280                 285

Asn Asn Arg Ala Ser Phe Ser Gln Tyr Gly Ala Gly Leu Asp Ile Val
290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Ala Ala
            325                 330                 335

Ala Leu Val Lys Gln Lys Asn Pro Ser Trp Ser Asn Val Gln Ile Arg
            340                 345                 350

Asn His Leu Lys Asn Thr Ala Thr Ser Leu Gly Ser Thr Asn Leu Tyr
            355                 360                 365

Gly Ser Gly Leu Val Asn Ala Glu Ala Ala Thr Arg
    370                 375                 380
```

<210> SEQ ID NO 28
<211> LENGTH: 380
<212> TYPE: PRT
<213> ORGANISM: Artificial
<220> FEATURE:
<223> OTHER INFORMATION: synthetic Bacillus variant

<400> SEQUENCE: 28

```
Val Arg Ser Lys Lys Leu Trp Ile Val Ala Ser Thr Ala Leu Leu Ile
1               5                   10                  15

Ser Val Ala Phe Ser Ser Ile Ala Ser Ala Glu Glu Ala Lys
            20                  25                  30

Arg Lys Tyr Leu Ile Gly Phe Asn Glu Gln Glu Ala Val Ser Glu Phe
        35                  40                  45

Val Glu Gln Val Glu Ala Asn Asp Glu Val Ala Ile Leu Ser Glu Glu
    50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110

Gln Ser Val Pro Trp Gly Ile Ser Arg Val Gln Ala Pro Ala Ala His
        115                 120                 125

Asn Arg Gly Leu Thr Gly Ser Gly Val Lys Val Ala Val Leu Asp Thr
130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190

Val Ala Pro Asn Ala Glu Leu Tyr Ala Val Lys Val Leu Gly Ala Ser
        195                 200                 205

Gly Ser Gly Ser Val Ser Ser Ile Ala Gln Gly Leu Glu Trp Ala Gly
    210                 215                 220

Asn Asn Val Met His Val Ala Asn Leu Ser Leu Gly Leu Gln Ala Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Gly Ser Ile Ser Tyr
            260                 265                 270

Pro Ala Arg Tyr Ala Asn Ala Met Ala Val Gly Ala Thr Asp Gln Asn
        275                 280                 285

Asn Asn Arg Ala Ser Phe Ser Gln Tyr Gly Ala Gly Leu Asp Ile Val
    290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Ala Ala
                325                 330                 335

Ala Leu Val Lys Gln Lys Asn Pro Ser Trp Ser Asn Val Gln Ile Arg
            340                 345                 350

Asn His Leu Lys Asn Thr Ala Ser Leu Gly Ser Thr Asn Leu Tyr
        355                 360                 365

Gly Ser Gly Leu Val Asn Ala Glu Ala Ala Thr Arg
    370                 375                 380
```

<210> SEQ ID NO 29
<211> LENGTH: 380
<212> TYPE: PRT
<213> ORGANISM: Artificial

```
<220> FEATURE:
<223> OTHER INFORMATION: synthetic Bacillus variant

<400> SEQUENCE: 29

Met Arg Ser Lys Lys Leu Trp Ile Val Ala Ser Thr Ala Leu Leu Ile
1               5                   10                  15

Ser Val Ala Phe Ser Ser Ser Ile Ala Ser Ala Ala Glu Glu Ala Lys
            20                  25                  30

Glu Lys Tyr Leu Ile Gly Phe Asn Glu Gln Glu Ala Val Ser Glu Phe
        35                  40                  45

Val Glu Gln Val Glu Ala Asn Asp Glu Val Ala Ile Leu Ser Glu Glu
    50                  55                  60

Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110

Gln Ser Val Pro Trp Gly Ile Ser Arg Val Gln Ala Pro Ala Ala His
        115                 120                 125

Asn Arg Gly Leu Thr Gly Ser Gly Val Lys Val Ala Val Leu Asp Thr
    130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190

Val Ala Pro Asn Ala Glu Leu Tyr Ala Val Lys Val Leu Gly Ala Ser
        195                 200                 205

Gly Gly Gly Ser Asn Ser Ser Ile Ala Gln Gly Leu Glu Trp Ala Gly
    210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Gly Ser Ile Ser Tyr
            260                 265                 270

Pro Ala Arg Tyr Ala Asn Ala Met Ala Val Gly Ala Thr Asp Gln Asn
        275                 280                 285

Asn Asn Arg Ala Ser Phe Ser Gln Tyr Gly Ala Gly Leu Asp Ile Val
    290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Ala Ala
                325                 330                 335

Ala Leu Val Lys Gln Lys Asn Pro Ser Trp Ser Asn Val Gln Ile Arg
            340                 345                 350

Asn His Leu Lys Asn Thr Ala Thr Ser Leu Gly Ser Thr Asn Leu Tyr
        355                 360                 365

Gly Ser Gly Leu Val Asn Ala Glu Ala Ala Thr Arg
    370                 375                 380

<210> SEQ ID NO 30
<211> LENGTH: 1143
```

```
<212> TYPE: DNA
<213> ORGANISM: Bacillus alcalophilus

<400> SEQUENCE: 30
atgaagaaac cgttggggaa aattgtcgca agcaccgcac tactcatttc tgttgctttt      60
agttcatcga tcgcatcggc tgctgaagaa gcaaaagaaa atatttaat tggctttaat      120 gagcaggaag ctgtcagtga gtttgtagaa caagtagagg caaatgacga ggtcgccatt     180
ctctctgagg aagaggaagt cgaaattgaa ttgcttcatg aatttgaaac gattcctgtt     240
ttatccgttg agttaagccc agaagatgtg gacgcgcttg aactcgatcc agcgatttct     300
tatattgaag aggatgcaga agtaacgaca atggcgcaat cagtgccatg gggaattagc     360
cgtgtgcaag ccccagctgc ccataaccgt ggattgacag gttctggtgt aaaagttgct     420
gtcctcgata caggtatttc cactcatcca gacttaaata ttcgtggtgg cgctagcttt     480
gtaccagggg aaccatccac tcaagatggg aatgggcatg gcacgcatgt ggctgggacg     540
attgctgctt taaacaattc gattggcgtt cttggcgtag caccgaacgc ggaactatac     600
gctgttaaag tattaggggc gagcggttca ggttcggtca gctcgattgc ccaaggattg     660
gaatgggcag ggaacaatgg catgcacgtt gctaatttga gtttaggaag cccttcgcca     720
agtgccacac ttgagcaagc tgttaatagc gcgacttcta gaggcgttct tgttgtagcg     780
gcatctggga attcaggtgc aggctcaatc agctatccgg cccgttatgc gaacgcaatg     840
gcagtcggag ctactgacca aaacaacaac cgcgccagct tttcacagta tggcgcaggg     900
cttgacattg tcgcaccagg tgtaaacgtg cagagcacat acccaggttc aacgtatgcc     960
agcttaaacg gtacatcgat ggctactcct catgttgcag gtgcagcagc ccttgttaaa     1020
caaaagaacc atcttggtc caatgtacaa atccgcaatc atctaaagaa tacggcaacg     1080
agcttaggaa gcacgaactt gtatggaagc ggacttgtca atgcagaagc ggcaacacgc     1140
taa                                                                   1143

<210> SEQ ID NO 31
<211> LENGTH: 1140
<212> TYPE: DNA
<213> ORGANISM: Bacillus clausii

<400> SEQUENCE: 31
gtgagaagca aaaaattgtg gatcgtcgcg tcgaccgcac tactcatttc tgttgctttt      60
agttcatcga tcgcatcggc tgctgaagaa gcaaaagaaa atatttaat tggctttaat      120 gagcaggaag ctgtcagtga gtttgtagaa caagtagagg caaatgacga ggtcgccatt     180
ctctctgagg aagaggaagt cgaaattgaa ttgcttcatg aatttgaaac gattcctgtt     240
ttatccgttg agttaagccc agaagatgtg gacgcgcttg aactcgatcc agcgatttct     300
tatattgaag aggatgcaga agtaacgaca atggcgcaat cggtaccatg gggaattagc     360
cgtgtgcaag ccccagctgc ccataaccgt ggattgacag gttctggtgt aaaagttgct     420
gtcctcgata caggtatttc cactcatcca gacttaaata ttcgtggtgg cgctagcttt     480
gtaccagggg aaccatccac tcaagatggg aatgggcatg gcacgcatgt ggctgggacg     540
attgctgctt taaacaattc gattggcgtt cttggcgtag caccgaacgc ggaactatac     600
gctgttaaag tattaggggc gagcggttca ggttcggtca gctcgattgc ccaaggattg     660
gaatgggcag ggaacaatgt tatgcacgtt gctaatttga gtttaggact gcaggcacca     720
agtgccacac ttgagcaagc tgttaatagc gcgacttcta gaggcgttct tgttgtagcg     780
gcatctggga attcaggtgc aggctcaatc agctatccgg cccgttatgc gaacgcaatg     840
```

```
gcagtcggag ctactgacca aaacaacaac cgcgccagct tttcacagta tggcgcaggg    900
cttgacattg tcgcaccagg tgtaaacgtg cagagcacat acccaggttc aacgtatgcc    960
agcttaaacg gtacatcgat ggctactcct catgttgcag gtgcagcagc ccttgttaaa   1020
caaaagaacc catcttggtc caatgtacaa atccgcaatc atctaaagaa tacggcaacg   1080
agcttaggaa gcacgaactt gtatggaagc ggacttgtca atgcagaagc ggcaacacgt   1140
```

```
<210> SEQ ID NO 32
<211> LENGTH: 1140
<212> TYPE: DNA
<213> ORGANISM: Artificial
<220> FEATURE:
<223> OTHER INFORMATION: synthetic Bacillus variant

<400> SEQUENCE: 32
gtgagaagca aaaaattgtg gatcgtcgcg tcgaccgcac tactcatttc tgttgctttt     60
agttcatcga tcgcatcggc tgctgaagaa gcaaaacaaa aatatttaat tggctttaat    120
gagcaggaag ctgtcagtga gtttgtagaa caagtagagg caaatgacga ggtcgccatt    180
ctctctgagg aagaggaagt cgaaattgaa ttgcttcatg aatttgaaac gattcctgtt    240
ttatccgttg agttaagccc agaagatgtg gacgcgcttg aactcgatcc agcgatttct    300
tatattgaag aggatgcaga agtaacgaca atggcgcaat cggtaccatg gggaattagc    360
cgtgtgcaag ccccagctgc ccataaccgt ggattgacag gttctggtgt aaaagttgct    420
gtcctcgata caggtatttc cactcatcca gacttaaata ttcgtggtgg cgctagcttt    480
gtaccagggg aaccatccac tcaagatggg aatgggcatg gcacgcatgt ggctgggacg    540
attgctgctt taaacaattc gattggcgtt cttggcgtag caccgaacgc ggaactatac    600
gctgttaaag tattaggggc gagcggttca ggttcggtca gctcgattgc ccaaggattg    660
gaatgggcag ggaacaatgt tatgcacgtt gctaatttga gtttaggact gcaggcacca    720
agtgccacac ttgagcaagc tgttaatagc gcgacttcta gaggcgttct tgttgtagcg    780
gcatctggga attcaggtgc aggctcaatc agctatccgg cccgttatgc gaacgcaatg    840
gcagtcggag ctactgacca aaacaacaac cgcgccagct tttcacagta tggcgcaggg    900
cttgacattg tcgcaccagg tgtaaacgtg cagagcacat acccaggttc aacgtatgcc    960
agcttaaacg gtacatcgat ggctactcct catgttgcag gtgcagcagc ccttgttaaa   1020
caaaagaacc catcttggtc caatgtacaa atccgcaatc atctaaagaa tacggcaacg   1080
agcttaggaa gcacgaactt gtatggaagc ggacttgtca atgcagaagc ggcaacacgt   1140
```

```
<210> SEQ ID NO 33
<211> LENGTH: 1140
<212> TYPE: DNA
<213> ORGANISM: Artificial
<220> FEATURE:
<223> OTHER INFORMATION: synthetic Bacillus variant

<400> SEQUENCE: 33
gtgagaagca aaaaattgtg gatcgtcgcg tcgaccgcac tactcatttc tgttgctttt     60
agttcatcga tcgcatcggc tgctgaagaa gcaaaacgca aatatttaat tggctttaat    120
gagcaggaag ctgtcagtga gtttgtagaa caagtagagg caaatgacga ggtcgccatt    180
ctctctgagg aagaggaagt cgaaattgaa ttgcttcatg aatttgaaac gattcctgtt    240
ttatccgttg agttaagccc agaagatgtg gacgcgcttg aactcgatcc agcgatttct    300
tatattgaag aggatgcaga agtaacgaca atggcgcaat cggtaccatg gggaattagc    360
```

-continued

```
cgtgtgcaag ccccagctgc ccataaccgt ggattgacag gttctggtgt aaaagttgct    420
gtcctcgata caggtatttc cactcatcca gacttaaata ttcgtggtgg cgctagcttt    480
gtaccagggg aaccatccac tcaagatggg aatgggcatg gcacgcatgt ggctgggacg    540
attgctgctt taaacaattc gattggcgtt cttggcgtag caccgaacgc ggaactatac    600
gctgttaaag tattaggggc gagcggttca ggttcggtca gctcgattgc ccaaggattg    660
gaatgggcag ggaacaatgt tatgcacgtt gctaatttga gtttaggact gcaggcacca    720
agtgccacac ttgagcaagc tgttaatagc gcgacttcta gaggcgttct tgttgtagcg    780
gcatctggga attcaggtgc aggctcaatc agctatccgg cccgttatgc gaacgcaatg    840
gcagtcggag ctactgacca aaacaacaac cgcgccagct tttcacagta tggcgcaggg    900
cttgacattg tcgcaccagg tgtaaacgtg cagagcacat acccaggttc aacgtatgcc    960
agcttaaacg gtacatcgat ggctactcct catgttgcag gtgcagcagc ccttgttaaa   1020
caaaagaacc catcttggtc caatgtacaa atccgcaatc atctaaagaa tacggcaacg   1080
agcttaggaa gcacgaactt gtatggaagc ggacttgtca atgcagaagc ggcaacacgt   1140
```

<210> SEQ ID NO 34
<211> LENGTH: 1143
<212> TYPE: DNA
<213> ORGANISM: Artificial
<220> FEATURE:
<223> OTHER INFORMATION: synthetic Bacillus variant

<400> SEQUENCE: 34

```
atgaagaaac cgttggggaa aattgtcgca agcaccgcac tactcatttc tgttgctttt     60
agttcatcga tcgcatcggc tgctgaagaa gcaaaagaaa aatatttaat tggctttaat    120
gagcaggaag ctgtcagtga gtttgtagaa caagtagagg caaatgacga ggtcgccatt    180
ctctctgagg aagaggaagt cgaaattgaa ttgcttcatg aatttgaaac gattcctgtt    240
ttatccgttg agttaagccc agaagatgtg gacgcgcttg aactcgatcc agcgatttct    300
tatattgaag aggatgcaga agtaacgaca atggcgcaat cggtaccatg gggaattagc    360
cgtgtgcaag ccccagctgc ccataaccgt ggattgacag gttctggtgt aaaagttgct    420
gtcctcgata caggtatttc cactcatcca gacttaaata ttcgtggtgg cgctagcttt    480
gtaccagggg aaccatccac tcaagatggg aatgggcatg gcacgcatgt ggctgggacg    540
attgctgctt taaacaattc gattggcgtt cttggcgtag caccgaacgc ggaactatac    600
gctgttaaag tattaggggc gagcggtggc ggttcgaaca gctcgattgc ccaaggattg    660
gaatgggcag ggaacaatgg catgcacgtt gctaatttga gtttaggaag cccttcgcca    720
agtgccacac ttgagcaagc tgttaatagc gcgacttcta gaggcgttct tgttgtagcg    780
gcatctggga attcaggtgc aggctcaatc agctatccgg cccgttatgc gaacgcaatg    840
gcagtcggag ctactgacca aaacaacaac cgcgccagct tttcacagta tggcgcaggg    900
cttgacattg tcgcaccagg tgtaaacgtg cagagcacat acccaggttc aacgtatgcc    960
agcttaaacg gtacatcgat ggctactcct catgttgcag gtgcagcagc ccttgttaaa   1020
caaaagaacc catcttggtc caatgtacaa atccgcaatc atctaaagaa tacggcaacg   1080
agcttaggaa gcacgaactt gtatggaagc ggacttgtca atgcagaagc ggcaacacgc   1140
taa                                                                 1143
```

<210> SEQ ID NO 35
<211> LENGTH: 252

<212> TYPE: DNA
<213> ORGANISM: Artificial
<220> FEATURE:
<223> OTHER INFORMATION: synthetic variant

<400> SEQUENCE: 35

```
gctgaagaag caaaacaaaa atatttaatt ggctttaatg agcaggaagc tgtcagtgag    60
tttgtagaac aagtagaggc aaatgacgag gtcgccattc tctctgagga agaggaagtc   120
gaaattgaat tgcttcatga atttgaaacg attcctgttt tatccgttga gttaagccca   180
gaagatgtgg acgcgcttga actcgatcca gcgatttctt atattgaaga ggatgcagaa   240
gtaacgacaa tg                                                       252
```

<210> SEQ ID NO 36
<211> LENGTH: 84
<212> TYPE: PRT
<213> ORGANISM: Artificial
<220> FEATURE:
<223> OTHER INFORMATION: synthetic variant

<400> SEQUENCE: 36

```
Ala Glu Glu Ala Lys Gln Lys Tyr Leu Ile Gly Phe Asn Glu Gln Glu
1               5                   10                  15
Ala Val Ser Glu Phe Val Glu Gln Val Glu Ala Asn Asp Glu Val Ala
            20                  25                  30
Ile Leu Ser Glu Glu Glu Val Glu Ile Glu Leu Leu His Glu Phe
        35                  40                  45
Glu Thr Ile Pro Val Leu Ser Val Glu Leu Ser Pro Glu Asp Val Asp
    50                  55                  60
Ala Leu Glu Leu Asp Pro Ala Ile Ser Tyr Ile Glu Glu Asp Ala Glu
65                  70                  75                  80
Val Thr Thr Met
```

<210> SEQ ID NO 37
<211> LENGTH: 252
<212> TYPE: DNA
<213> ORGANISM: Artificial
<220> FEATURE:
<223> OTHER INFORMATION: synthetic variant

<400> SEQUENCE: 37

```
gctgaagaag caaaacgcaa atatttaatt ggctttaatg agcaggaagc tgtcagtgag    60
tttgtagaac aagtagaggc aaatgacgag gtcgccattc tctctgagga agaggaagtc   120
gaaattgaat tgcttcatga atttgaaacg attcctgttt tatccgttga gttaagccca   180
gaagatgtgg acgcgcttga actcgatcca gcgatttctt atattgaaga ggatgcagaa   240
gtaacgacaa tg                                                       252
```

<210> SEQ ID NO 38
<211> LENGTH: 84
<212> TYPE: PRT
<213> ORGANISM: Artificial
<220> FEATURE:
<223> OTHER INFORMATION: synthetic variant

<400> SEQUENCE: 38

```
Ala Glu Glu Ala Lys Arg Lys Tyr Leu Ile Gly Phe Asn Glu Gln Glu
1               5                   10                  15
Ala Val Ser Glu Phe Val Glu Gln Val Glu Ala Asn Asp Glu Val Ala
            20                  25                  30
```

```
Ile Leu Ser Glu Glu Glu Val Glu Ile Glu Leu Leu His Glu Phe
        35                  40                  45

Glu Thr Ile Pro Val Leu Ser Val Glu Leu Ser Pro Glu Asp Val Asp
    50                  55                  60

Ala Leu Glu Leu Asp Pro Ala Ile Ser Tyr Ile Glu Glu Asp Ala Glu
65                  70                  75                  80

Val Thr Thr Met

<210> SEQ ID NO 39
<211> LENGTH: 46
<212> TYPE: DNA
<213> ORGANISM: Bacillus subtilis

<400> SEQUENCE: 39
tgggtctact aaaatattat tccatctatt acaataaatt cacaga          46

<210> SEQ ID NO 40
<211> LENGTH: 46
<212> TYPE: DNA
<213> ORGANISM: Artificial
<220> FEATURE:
<223> OTHER INFORMATION: synthetic Bacillus mutant

<400> SEQUENCE: 40
tgggtcttga caaatattat tccatctatt acaataaatt cacaga          46

<210> SEQ ID NO 41
<211> LENGTH: 4
<212> TYPE: PRT
<213> ORGANISM: Artificial
<220> FEATURE:
<223> OTHER INFORMATION: synthetic reagent

<400> SEQUENCE: 41

Ala Ala Pro Phe
1
```

MODIFIED SECRETION SYSTEM TO INCREASE EXPRESSION OF POLYPEPTIDES IN BACTERIA

CROSS REFERENCE TO RELATED APPLICATIONS

This application claims priority to U.S. Ser. No. 60/928,875 filed on May 10, 2007, which is herein incorporated by reference in its entirety.

SEQUENCE LISTING

The sequence listing submitted via EFS, in compliance with C.F.R. §1.52(e), is incorporated herein by reference. The sequence listing text file submitted via EFS contains the file "30975US_SeqListing.TXT", created on Jun. 8, 2012, which is 37,444 bytes in size.

FIELD OF THE INVENTION

The present invention provides methods of altering the production of desired polypeptides in a host cell. In particular, the present invention provides polynucleotides encoding truncated SecG proteins capable of facilitating the secretion of desired proteases by a bacterial host cell, such as *Bacillus* species, as well as expression vectors and a host cell containing the polynucleotides.

BACKGROUND

Gram-positive microorganisms, such as members of the genus *Bacillus*, are useful for large-scale industrial fermentation due, in part, to their ability to secrete their fermentation products into culture media. Secreted proteins are exported across a cell membrane and a cell wall, and then are subsequently released into the external media. Secretion of polypeptides into periplasmic space or into the culture media is an important subject that needs to be carefully considered in industrial fermentations.

Secretion of heterologous polypeptides from microorganisms is a widely used technique in industry. Typically, cells can be transformed with a nucleic acid encoding a heterologous polypeptide of interest. These transformed cells can then express the heterologous polypeptide of interest and thus secrete it in large quantities. This technique can be used to produce a greater amount of polypeptide than that which would be produced naturally. These expressed polypeptides have a number of industrial applications, including therapeutic and agricultural uses, as well as use in foods, cosmetics, cleaning compositions, animal feed, etc. There is a need in the field to provide hosts capable of secreting heterologous polypeptides.

SUMMARY OF THE INVENTION

The present invention provides methods of altering the production of desired polypeptides in a host cell. In particular, the present invention provides polynucleotides encoding truncated SecG proteins capable of facilitating the secretion of desired proteases by a bacterial host cell, such as *Bacillus* species, as well as expression vectors and a host cell containing the polynucleotides.

The present teachings are based, at least in part, on the discovery that certain proteins involved in the secretion of heterologous polypeptides in a bacterial polypeptide secretion system can be modified and still retain their function(s), e.g., certain proteins can be truncated, mutated or deleted and still retain or even increase their ability to facilitate polypeptide secretion. Accordingly the present teachings provide polypeptides, including their encoding polynucleotides, capable of facilitating the secretion of a desired polypeptide by a host bacterial system. In addition, the present teachings provide methods of using these polypeptides in a bacterial system to produce heterologous polypeptides.

In one embodiment, the invention provides an isolated heterologous polynucleotide that encodes a heterologous truncated SecG, which is capable of facilitating the secretion of a desired polypeptide by a bacterial host cell. In some embodiments, the gene encoding for the endogenous SecG of the bacterial host cell is replaced by the heterologous polynucleotide, while in other embodiments, the gene encoding for the endogenous SecG of the bacterial host cell is complemented by the heterologous polynucleotide. In yet other embodiments, the heterologous polypeptide that encodes the truncated SecG comprises at least about 50% identity with the truncated SecG of SEQ ID NO:11. In some embodiments, the truncated SecG includes a region of a full-length heterologous SecG, which, in some embodiments, comprises the first N-terminal 39 amino acids of the full-length SecG polypeptide. In some other embodiments the truncated SecG comprises the first transmembrane domain of said SecG. In another embodiment, the invention provides an isolated heterologous polynucleotide that encodes a heterologous truncated SecG that comprises the first 39 amino acids of any one of the SecG of SEQ ID NOS:1-9, and that is capable of facilitating the secretion of a desired polypeptide by a bacterial host cell. In other embodiments, the SecG of the invention is a bacterial SecG. The invention encompasses SecG proteins that are from a *Bacillus* sp or a *Geobacillus*.

In another embodiment, the invention provides an expression vector containing an isolated heterologous polynucleotide that encodes a heterologous truncated SecG, which is capable of facilitating the secretion of a desired polypeptide by a bacterial host cell.

In another embodiment, the invention provides a polypeptide encoding an isolated heterologous polynucleotide that encodes a heterologous truncated SecG, which is capable of facilitating the secretion of a desired polypeptide by a bacterial host cell.

In another embodiment, the invention provides a method for producing a desired polypeptide in a bacterial host cell comprising: (a) expressing a heterologous SecG polypeptide in said bacterial host cell, and (b) producing said desired polypeptide. In one embodiment, the heterologous SecG is encoded by a truncated gene that replaces the endogenous secG gene of the host cell. In another embodiment, the heterologous SecG is encoded by a full-length gene that replaces the endogenous secG gene of the host cell. In yet another embodiment, the heterologous SecG is a truncated polypeptide that comprises the first 39 amino acids of the full-length amino acid sequence chosen from SEQ ID NOS: 1-9. In some embodiments, the truncated SecG contains only one transmembrane region. In another embodiment, the invention provides a method for producing a bacterial alkaline serine protease that is at least 80% identical to the alkaline serine protease of SEQ ID NO:26 in a bacterial host cell comprising: (a) expressing a heterologous SecG polypeptide in the bacterial host cell, and (b) producing the bacterial alkaline serine protease. In some embodiments, the bacterial host cell does not express the endogenous SecG protein, while in other embodiments, the host cell expresses endogenous SecG. In yet other embodiments, the heterologous SecG is capable of increasing the amount of the desired polypeptide produced by the host cell as compared to the amount of the desired polypeptide produced by a corresponding host cell that does not express the heterologous SecG. In some embodiments, the invention provides a method for producing a desired polypeptide in a bacterial host cell comprising: (a) expressing a heterologous SecG polypeptide in said bacterial host cell, (b) producing said desired polypeptide and further comprising recovering said desired polypeptide. In some embodiments, the desired polypeptide and the heterologous SecG are derived from a first strain, and wherein the first strain is different from that of the host cell. In some embodiments, the first strain is *B. clausii* and the host cell is *B. subtilis*. In other embodiments, the endogenous SecG gene of said host cell is deleted. In another embodiment, the invention provides a bacterial host cell comprising a polynucleotide encoding a heterologous SecG, wherein the heterologous SecG is capable of increasing the secretion of a desired polypeptide by the host cell when compared to the secretion of the desired polypeptide by a corresponding host cell that does not express the heterologous SecG. In one embodiment, the bacterial host cell is a *Bacillus* sp. host cell. In another embodiment, the bacterial host cell is a *B. subtilis* host cell. In another embodiment, the desired protein secreted by the bacterial host cell is an enzyme. In some embodiments, the enzyme is a serine protease. In other embodiments, the desired polypeptide is chosen from the proteases of SEQ ID NOS:25-29, 36 and 28, or variants thereof. In some embodiments, the endogenous secG gene of the host cell is deleted. In other embodiments, the endogenous secG gene of said the cell is complemented by the heterologous secG gene encoding the heterologous SecG. In other embodiments, the endogenous secG gene of the host cell is replaced by a heterologous secG gene encoding said heterologous SecG. In some embodiments, the heterologous SecG is truncated, while in other embodiments, the heterologous SecG is a full-length SecG.

These and other features of the present teachings are set forth below.

BRIEF DESCRIPTION OF THE DRAWINGS

The skilled artisan will understand that the drawings are for illustration purposes only. The drawings are not intended to limit the scope of the present teachings in any way.

DETAILED DESCRIPTION OF THE INVENTION

Figure 1:
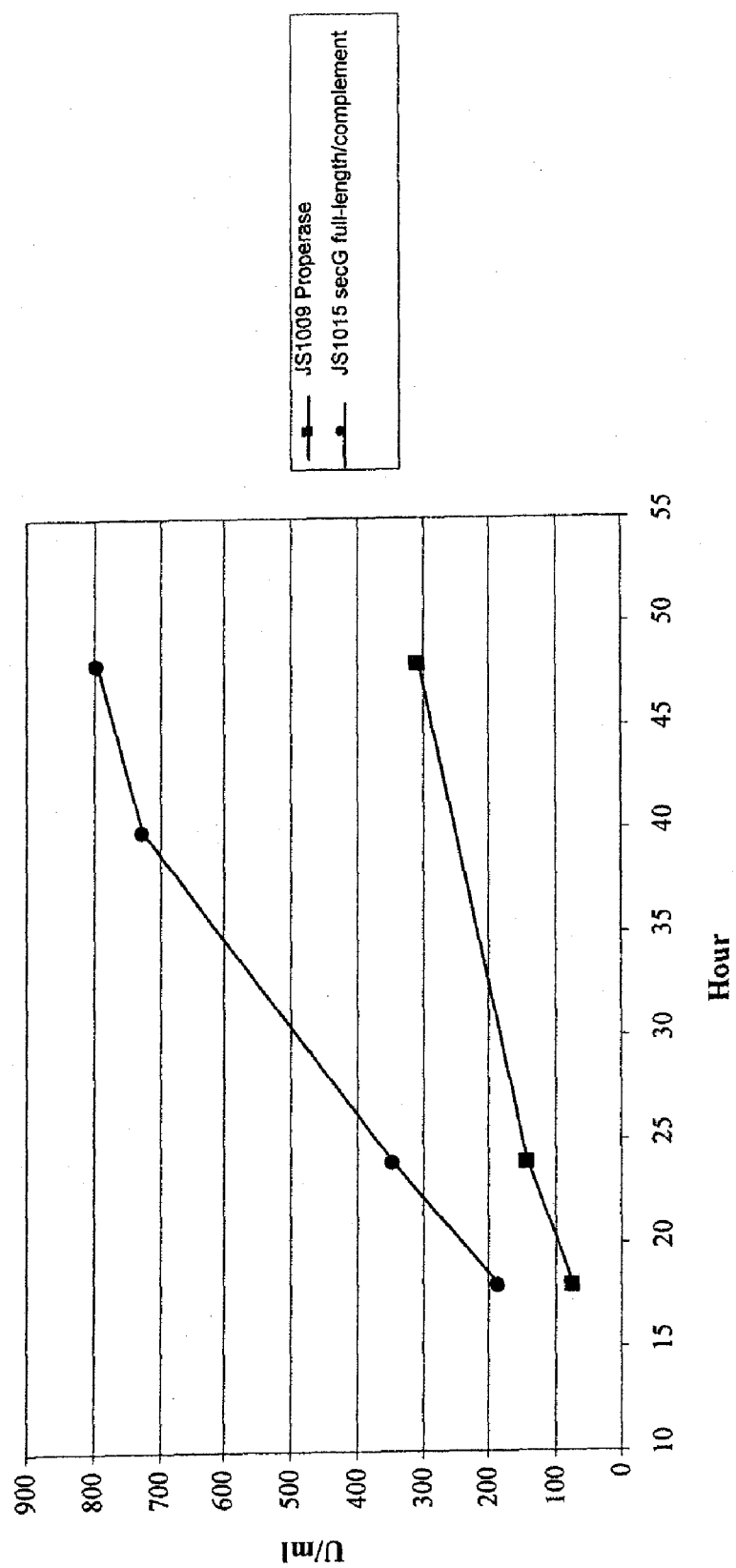
FIG. 1 shows the increase in Properase production by *B. substilis* host cells (JS1015) in which a polynucleotide encoding a truncated SecG from *B. clausii* (SEQ ID NO:12) is integrated into the *B. subtilis* chromosome to complement the endogenous *B. subtilis* secG when compared to the production of Properase in the control host cells (JS1009), which do not comprise the truncated *B. clausii* secG gene.

The present invention provides methods of altering the production of desired polypeptides in a host cell. In particular, the present invention provides polynucleotides encoding full-length and truncated SecG proteins capable of facilitating the secretion of desired proteases by a bacterial host cell, such as *Bacillus* species, as well as expression vectors and host cells containing the polynucleotides.

The present teachings will now be described in detail by way of reference only using the following definitions and examples. Unless defined otherwise herein, all technical and scientific terms used herein have the same meaning as commonly understood by one of ordinary skill in the art to which this invention belongs. Numeric ranges are inclusive of the numbers defining the range. The headings provided herein are not limitations of the various aspects or embodiments which can be had by reference to the specification as a whole. Accordingly, the terms defined immediately below are more fully defined by reference to the specification as a whole.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous texts and reference works (See e.g., Sambrook et al., "Molecular Cloning: A Laboratory Manual", Second Edition (Cold Spring Harbor), [1989]); and Ausubel et al., "Current Protocols in Molecular Biology" [1987]). All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. For example, Singleton and Sainsbury, Dictionary of Microbiology and Molecular Biology, 2d Ed., John Wiley and Sons, NY (1994); and Hale and Markham, The Harper Collins Dictionary of Biology, Harper Perennial, NY (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular "a", "an" and "the" includes the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Furthermore, the headings provided herein are not limitations of the various aspects or embodiments of the invention, which can be had by reference to the specification as a whole. Accordingly, the terms defined immediately below are more fully defined by reference to the specification as a whole. Nonetheless, in order to facilitate understanding of the invention, a number of terms are defined below.

Definitions

The term "polypeptide" as used herein refers to a compound made up of a single chain of amino acid residues linked by peptide bonds. The term "protein" as used herein is used interchangeably with the term "polypeptide."

The terms "nucleic acid" and "polynucleotide" are used interchangeably and encompass DNA, RNA, cDNA, single stranded or double stranded and chemical modifications thereof. Because the genetic code is degenerate, more than one codon may be used to encode a particular amino acid, and the present invention encompasses all polynucleotides, which encode a particular amino acid sequence.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express nucleic acids or polypeptides that are not found within the native (non-recombinant) form of the cell or express native genes that are otherwise abnormally expressed, under expressed, over expressed or not expressed at all.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, the term "native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. In some embodiments, a chimeric gene is an endogenous gene operably linked to a promoter that is not its native promoter.

As used herein, the term "endogenous gene" refers to a native gene in its natural location in the genome of an organism. A "foreign" or an "exogenous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, a "fusion nucleic acid" comprises two or more nucleic acids operably linked together. The nucleic acid may be DNA, both genomic and cDNA, or RNA, or a hybrid of RNA and DNA. Nucleic acid encoding all or part of the sequence of a polypeptide can be used in the construction of the fusion nucleic acid sequences. In some embodiments, nucleic acid encoding full length polypeptides are used. In some embodiments, nucleic acid encoding a portion of the polypeptide may be employed.

The term "chimeric polypeptide" and "fusion polypeptide" are used interchangeably herein and refer to a protein that comprises at least two separate and distinct regions that may or may not originate from the same protein. For example, a signal peptide linked to the protein of interest wherein the signal peptide is not normally associated with the protein of interest would be termed a chimeric polypeptide or chimeric protein.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

As used herein, the term "operably linked" means that the transcriptional and translational regulatory nucleic acid is positioned relative to the coding sequences in such a manner that transcription is initiated. Generally, this will mean that the promoter and transcriptional initiation or start sequences are positioned 5' to the coding region. The transcriptional and translational regulatory nucleic acid will generally be appropriate to the host cell used to express the protein. Numerous types of appropriate expression vectors, and suitable regulatory sequences are known in the art for a variety of host cells.

As used herein, the term "expression" refers to the process by which a polypeptide is produced based on the nucleic acid sequence of a gene. The process includes both transcription and translation.

The terms "production" and "secretion" with reference to a desired protein e.g. a protease, encompass the processing steps of a full-length protease including: the removal of the signal peptide, which is known to occur during protein secretion; the removal of the pro region, which creates the active mature form of the enzyme and which is known to occur during the maturation process (Wang et al., Biochemistry 37:3165-3171 (1998); Power et al., Proc Natl Aced Sci USA 83:3096-3100 (1986)), and the translocation of the protease to the outside of the host cell.

The term "processing or "processed" with reference to a protease refers to the maturation process that a full-length protein e.g. a protease, undergoes to become an active mature enzyme.

As used herein, the term "chromosomal integration" refers to the process whereby an incoming sequence is introduced into the chromosome of a host cell. The homologous regions of the transforming DNA align with homologous regions of the chromosome. Subsequently, the sequence between the homology boxes is replaced by the incoming sequence in a double crossover (i.e., homologous recombination). In some embodiments of the present invention, homologous sections of an inactivating chromosomal segment of a DNA construct align with the flanking homologous regions of the indigenous chromosomal region of the *Bacillus* chromosome. Subsequently, the indigenous chromosomal region is deleted by the DNA construct in a double crossover (i.e., homologous recombination). The deleted region can be simultaneously replaced with a different incoming chromosomal region.

"Homologous recombination" means the exchange of DNA fragments between two DNA molecules or paired chromosomes at the site of identical or nearly identical nucleotide sequences.

The term "replaced" or "replacing" with reference to an endogenous gene or protein e.g. secG gene, herein refers to a process whereby the endogenous secG gene of a host cell is no longer expressed as it is replaced by a heterologous polynucleotide from which a heterologous secG is expressed.

As used herein, "to complement", "complementation" or "complementing" are used interchangeably and refer to the contribution of two alleles on a phenotype. The terms herein refer to the presence of both the native or endogenous polynucleotides encoding the endogenous SecG, and the heterologous polynucleotides encoding the heterologous SecG, (in their entirety or fragments of them) are present in the same strain, either in the chromosome, naturally or by mean of integration, or carried in a multicopy plasmid. Thus, in some embodiments, a bacterial host cell comprises a heterologous polynucleotide encoding a heterologous SecG that complements the endogenous polynucleotide encoding the endogenous SecG, and resulting in a bacterial host cell that comprises two polynucleotides encoding SecG proteins. In some embodiments, the endogenous and heterologous SecG proteins are full-length SecG proteins. In other embodiments, the heterologous SecG is a truncated SecG protein.

The term "% homology" is used interchangeably herein with the term "% identity" herein and refers to the level of nucleic acid or amino acid sequence identity between the nucleic acid or amino acid sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, about 50, about 60, about 65, about 70, about 75, about 80, about 85, about 90, about 95, about 98, about 99% or more sequence identity to a given sequence. This homology is determined using standard techniques known in the art (See e.g., Smith and Waterman, Adv Appl Math, 2:482, 1981; Needleman and Wunsch, J Mol Biol, 48:443, 1970; Pearson and Lipman, Proc Natl Acad Sci USA, 85:2444, 1988; programs such as GAP, BESTFIT, FASTA, and TFASTA in the Wisconsin Genetics Software Package, Genetics Computer Group, Madison, Wis.; and Devereux et al., Nucl Acid Res, 12:387-395, 1984).

One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (Feng and Doolittle, J Mol Evol, 35:351-360, 1987). The method is similar to that described by Higgins and Sharp (Higgins and Sharp, CABIOS 5:151-153, 1989). Useful PILEUP parameters including a default gap weight of 3.00, a default gap length weight of 0.10, and weighted end gaps.

Another example of a useful algorithm is the BLAST algorithm, described by Altschul et al., (Altschul et al., J Mol Biol, 215:403-410, 1990; and Karlin et al., Proc Natl Acad Sci USA, 90:5873-5787, 1993). A particularly useful BLAST program is the WU-BLAST-2 program (See, Altschul et al., Meth Enzymol, 266:460-480, 1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid or amino acid sequence identity" is defined as the percentage of nucleotide residues in a candidate sequence that are identical to the nucleotide or amino acid residues of the starting sequence (i.e., the sequence of interest); and "percent amino acid sequence similarity" is defined as the percentage of amino acid residues in a candidate sequence that are identical to the amino acid residues of the starting sequence (i.e., the sequence of interest). A preferred method utilizes the BLASTN module of WU-BLAST-2 set to the default parameters, with overlap span and overlap fraction set to 1 and 0.125, respectively.

As used herein, "*Bacillus* sp." includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Graciliacillus, Halobacillus, Paenibacillus, Salibacillus, Thermobacillus, Ureibacillus*, and *Virgibacillus*.

"Naturally-occurring" or "wild-type" refers to a protease or a polynucleotide encoding a protease having the unmodified amino acid sequence identical to that found in nature. Naturally occurring enzymes include native enzymes, those enzymes naturally expressed or found in the particular microorganism. A sequence that is wild-type or naturally-occurring refers to a sequence from which a variant is derived. The wild-type sequence may encode either a homologous or heterologous protein.

As used herein, the term "heterologous protein" refers to a protein or polypeptide that does not naturally occur in the host cell. Similarly, a "heterologous polynucleotide" refers to a polynucleotide that does not naturally occur in the host cell.

As used herein, "homologous protein" or "endogenous protein" refer to a protein or polypeptide native or naturally occurring in a cell. Similarly, a "homologous polynucleotide" or "endogenous polynucleotide" refer to a polynucleotide that is native or naturally occurring in a cell.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

Related (and derivative) proteins comprise "variant proteins." In some preferred embodiments, variant proteins differ from a parent or precursor protein and one another by a small number of amino acid residues. As used herein, "variant" refers to a precursor protein which differs from its corresponding wild-type protein by the addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. A variant protein in the context of the present invention is exemplified by the *B. clauisii* protease V049 (SEQ ID NO:26), which is a variant of the naturally-occurring protein Maxacal (SEQ ID NO:25). In some preferred embodiments, variant proteins differ from a parent or precursor protein and one another by a small number of amino acid residues. The number of differing amino acid residues may be one or more, preferably 1, 2, 3, 4, 5, 10, 15, 20, 30, 40, 50, or more amino acid residues. In some preferred embodiments, the number of different amino acids between variants is between 1 and 10. In some particularly preferred embodiments, related proteins and particularly variant proteins comprise at least about 35%, about 40%, about 45%, about 50%, about 55%, about 60%, about 65%, about 70%, about 75%, about 80%, about 85%, about 90%, about 95%, about 97%, about 98%, or about 99% amino acid sequence identity. Additionally, a related protein or a variant protein as used herein refers to a protein that differs from another related protein or a parent protein in the number of prominent regions. For example, in some embodiments, variant proteins have 1, 2, 3, 4, 5, or 10 corresponding prominent regions that differ from the parent protein.

As used herein, the term "vector" refers to a polynucleotide construct designed to introduce nucleic acids into one or more cell types. Vectors include cloning vectors, expression vectors, shuttle vectors, plasmids, cassettes and the like.

As used herein, the term "expression vector" refers to a vector that has the ability to incorporate and express heterologous DNA fragment in a foreign cell. Many prokaryotic and eukaryotic expression vectors are commercially available.

As used herein, the terms "DNA construct," "transforming DNA" and "expression vector" are used interchangeably to refer to DNA used to introduce sequences into a host cell or organism. The DNA may be generated in vitro by PCR or any other suitable technique(s) known to those in the art, for example using standard molecular biology methods described in Sambrook et al. In addition, the DNA of the expression construct could be artificially, for example, chemically synthesized. The DNA construct, transforming DNA or recombinant expression cassette can be incorporated into a plasmid, chromosome, mitochondrial DNA, plastid DNA, virus, or nucleic acid fragment. Typically, the recombinant expression cassette portion of an expression vector, DNA construct or transforming DNA includes, among other sequences, a nucleic acid sequence to be transcribed and a promoter. In some embodiments, expression vectors have the ability to incorporate and express heterologous DNA fragments in a host cell.

The term "introduced" in the context of inserting a nucleic acid sequence into a cell, means "transfection" or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

By the term "host cell" is meant a cell into which a vector, or a chromosomally integrated expression cassette, or an integrated PCR fragment, has been introduced, and supports the replication, and/or transcription or transcription and translation (expression) of the expression construct.

A "corresponding host cell" is a host cell into which a vector, or a chromosomally integrated expression cassette, or an integrated PCR fragment, has not been introduced, and does not support the replication, and/or transcription or transcription and translation (expression) of the expression construct of a host cell. A "corresponding host cell" is the reference cell for a host cell.

The term "signal sequence" refers to a sequence of amino acids at the N-terminal portion of a protein which facilitates the secretion of the mature form of the protein outside the cell. The mature form of the extracellular protein lacks the signal sequence which is cleaved off during the secretion process. In some embodiments, the signal sequence is the sec-dependent signal peptides derived from *Bacillus*.

The terms "recovered", "isolated", and "separated" are used interchangeably herein to refer to a protein, cell, nucleic acid, amino acid etc. that is removed from at least one component with which it is naturally associated.

As used herein, the term "hybrid" refers to a sequence (e.g., a secretion factor) containing sequences derived from two or more orthologs. Thus, a "hybrid gene" or "hybrid protein" is a gene or protein, respectively, in which two or more fragment sequences are derived from 1) two or more different genes or proteins, respectively, 2) genes or proteins from two or more different organisms, or a combination thereof. For example, a hybrid gene or protein can contain two or more fragments from the same or different microorganisms, e.g., bacterial strains such as *Bacillus* strains or *Geobacillus* strains.

As used herein, the terms "protease," and "proteolytic activity" refer to a protein or peptide exhibiting the ability to hydrolyze peptides or substrates having peptide linkages. Many well known procedures exist for measuring proteolytic activity (Kalisz, "Microbial Proteinases," In: Fiechter (ed.), *Advances in Biochemical Engineering/Biotechnology*, [1988]). For example, proteolytic activity may be ascertained by comparative assays which analyze the produced protease's ability to hydrolyze a commercial substrate. Exemplary substrates useful in such analysis of protease or proteolytic activity, include, but are not limited to di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011; and U.S. Pat. No. 6,376,450, both of which are incorporated herein by reference. The AAPF assay (See e.g., Del Mar et al., Anal. Biochem., 99:316-320 [1979]) also finds use in determining the production of protease. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm on a spectrophotometer and is proportional to the active enzyme concentration.

As used herein, "ortholog" and "orthologous genes" refer to genes in different species that have evolved from a common ancestral gene by speciation. In general, orthologs retain the same function in during the course of evolution.

A "desired polypeptide", or "polypeptide of interest," refers to the protein/polypeptide to be expressed and secreted by the host cell. The protein of interest may be any protein that up until now has been considered for expression in prokaryotes and/or eukaryotes. In one embodiment, the protein of interest which is translocated by the secretion-associated proteins or systems utilized by the host cell include proteins comprising a signal peptide. The desired polypeptide may be either homologous or heterologous to the host. In some embodiments, the desired polypeptide is a secreted polypeptide, particularly an enzyme which is selected from amylolytic enzymes, proteolytic enzymes, cellulytic enzymes, oxidoreductase enzymes and plant wall degrading enzymes. In further embodiments, these enzyme include amylases, proteases, xylanases, lipases, laccases, phenol oxidases, oxidases, cutinases, cellulases, hemicellulases, esterases, perioxidases, catalases, glucose oxidases, phytases, pectinases, glucosidases, isomerases, transferases, galactosidases and chitinases. In still further embodiments, the desired polypeptide is a hormone, growth factor, receptor, vaccine, antibody, or the like. While it is not intended that the present invention be limited to any particular protein/polypeptide, in some most preferred embodiments, the desired polypeptide is a protease.

The present teachings are based on the discovery that certain proteins involved in the secretion of polypeptides in a bacterial secretion system can be modified while not diminishing the secretory function of the secretory complex. In some embodiments, secretory proteins can be truncated, mutated or deleted while the secretion system retains or even increase its ability to facilitate polypeptide secretion. Accordingly, the invention provides host bacterial systems and polypeptides and their encoding polynucleotides that are useful for facilitating the secretion of a desired polypeptide in a bacterial system. In addition, the present teachings provide methods for using these host bacterial systems and polypeptides to produce desired polypeptides, e.g., heterologous polypeptides. In some embodiments, the truncated secretory protein SecG increases the production of a desired protein In some aspects, the present teachings provide a polynucleotide encoding a truncated SecG. According to the present teaching, the truncated SecG can be any fragment of a full-length SecG, e.g., capable of facilitating the secretion of a desired polypeptide by a host bacterial cell. In some embodiments, the truncated SecG provided by the present teaching has an activity to or is capable of facilitating the secretion of a desired polypeptide by a host bacterial cell that contains a full-length endogenous SecG, a truncated or mutated endogenous SecG, or does not contain any portion of endogenous SecG. In some embodiments, the truncated SecG provided by the present invention includes one or more regions, e.g., contiguous or non-contiguous from one or more full-length SecGs. In some embodiments, the truncated SecG provided by the present invention includes a region of a full-length, wild-type SecG. In some embodiments, it includes a region of a full-length, variant, modified or mutated SecG.

In some embodiments, the truncated SecG contains a region of a full-length SecG selected from: a *B. clausii*, *B. subtilis*, *B. licheniformis*, *Geobacillus stearothermophilus*, *B. lentus Escherichia coli* or *B. amyloliquefaciens* SecG. In some embodiments, the truncated SecG contains a region of any of the exemplary full-length SecG e.g. SEQ ID NO: 1-SEQ ID NO: 9.

Amino Acid Sequence of *Geobacillus thermodenitrificans* NG80-2 (accession No. YP_001127090)

```
                                          (SEQ ID NO: 1)
MHALLVTLLVIVSIALIAIVLLQSGRSAGLSGAITGGAEQLFGKQKARGL

DAVFQRVTVVLAILYFVLTILVAYVQPS
```

Amino Acid Sequence of *Listeria welshimeri serovar* 6b str. SLCC5334; (Accession No. YP_850596)

```
                                          (SEQ ID NO: 2)
MSTVLTVLLIIVSVLLITVIILQPGKSAGLSGAISGGAEQLFGKQKARGL

ELILHRTTIVLSVVFFVILIALAYFVQ
```

Amino Acid Sequence of *Bacillus licheniformis* ATCC 14580 (DSM 13); (accession No. YP_080735)

```
                                          (SEQ ID NO: 3)
MAAFLTVLLVIVSIVLIVVVLLQSGKSAGLSGAISGGAEQLFGKQKARGL

DLILHRMTVVLTVLFFFLTIALAYFV
```

Amino Acid Sequence of *Bacillus subtilis* subsp. *subtilis* str. 168; (Accession No. NP_391243)

(SEQ ID NO: 4)
MHAVLITLLVIVSIALIIVVLLQSSKSAGLSGAISGGAEQLFGKQKARGL

DLILHRITVVLAVLFFVLTIALAYIL

Amino Acid Sequence of *Lactobacillus plantarum* WCFS1; (Accession No. NP_784540)

(SEQ ID NO: 5)
MYNLLLTLILVVSVLIIIAVMMQPSKTNDAMSSLTGGADDLFAKQKPRGF

EAFMQKVTVVLGIAFFILALALAWYSSK

Amino Acid Sequence of *Lactobacillus casei* ATCC 334; (Accession No. YP_806214)

(SEQ ID NO: 6)
MQSLLTTFLVIDSILIVIATLMQPSKQQDALSALSGGATDLFGKTKSRGF

EAFMEKVTVALGVIFFGLAIALVYLEAH

Amino Acid Sequence of *Staphylococcus aureus* subsp. *aureus* MRSA252; (Accession No. YP_040260)

(SEQ ID NO: 7)
MHTFLIVLLIIDCIALITVVLLQEGKSSGFSGAISGGAEQLFGKQKQRGV

DLFLNRLTIILSILFFVLMICISYLGM

Amino Acid Sequence of *Escherichia coli* K12; (Accession No. NP_417642)

(SEQ ID NO: 8)
MYEALLVVFLIVAIGLVGLIMLQQGKGADMGASFGAGASATLFGSSGSGN

FMTRMTALLATLFFIISLVLGNINSNKTNKGSEWENLSAPAKTEQTQPAA

PAKPTSDIPN

In other embodiments, the truncated SecG comprises a region of full-length *B. clausii* SecG of SEQ ID NO:9. The region of the truncated SecG capable of facilitating the secretion of a desired protein from a bacterial host cell comprises the N-terminal amino acid sequence that spans the first transmembrane region. In yet other embodiments, the truncated SecG has the sequence of SEQ ID NO:11.

Amino Acid Sequence of the Full-Length *B. clausii* SecG (SEQ ID NO: 9)
MQLFLMIALIIVSVLLVAVVLLQPGRSSGLSGAITGGAEQLLGKQKARGL

DAVLHRATIVLAVLFFILTGLNAYFL

Amino Acid Sequence of the Truncated *B. clausii* SecG (SEQ ID NO: 11)
MQLFLMIALIIVSVLLVAVVLLQPGRSSGLSGAITGGAE In some embodiments, the truncated SecG includes a region of a full-length SecG from any organism with a full-length SecG that has an amino acid sequence identical or substantially identical, e.g., at least about 50%, about 55%, about 60%, about 65%, about 70%, about 75%, about 80%, about 85%, about 90%, about 95%, about 98% or about 99% identical to the SecG sequences from *B. clausii, B. subtilis, B. licheniformis, Geobacillus stearothermophilus, B. lentus, Escherichia coli* or *B. amyloliquefaciens*. In other embodiments, the truncated SecG shares an amino acid sequence that is at least about 50%, about 55%, about 60%, about 65%, about 70%, about 75%, about 80%, about 85%, about 90%, about 95%, about 98% or about 99% similarity to the SecG sequences from *B. clausii, B. subtilis, B. licheniformis, Geobacillus stearothermophilus, B. lentus, Escherichia coli* or *B. amyloliquefaciens*. In yet other embodiments, the truncated SecG is at least 50% identical to the truncated SecG of SEQ ID NO:11.

In some embodiments, the truncated SecG includes a region of a full-length wild-type or full-length variant bacterial SecG. The full-length SecG can be derived from any bacterial strain now known, or later discovered, e.g., associated with polypeptide secretion pathway in a bacterial system. In some embodiments, the bacterial SecG is a *Bacillus* SecG. Examples of strains of bacteria from which the full-length SecG is selected include, but are not limited to, *Acinetobacter, Agrobacterium tumefaciens, Azoarcus, Bacillus anthracis, Bacillus clausii, Bacillus licheniformis, Bacillus amyloliquefaciens, Bacillus subtilis, Bacillus lentus, Bacillus halodurans Bifidobacterium longum, Buchnera aphidicola, Campestris, Campylobacter jejuni, Clostridium perfringens, Escherichia coli, Erwinia carotovora, Francisella tularensis, Haemophilus influenzae, Helicobacter pylori, Mycobacterium tuberculosis, Neisseria meningitides, Pseudomonas aeruginosa, Prochlorococcus marinus, Streptococcus pneumoniae, Salmonella enterica, Shewanella oneidensis, Salmonella enterica, Salmonella typhimurium, Staphylococcus epidermidis, Staphylococcus aureus, Shigella flexneri, Streptomyces coelicolor, Streptomyces lividans, Tropheryma whipplei, Tularensis, Temecula, Thermosynechococcus elongates, Thermococcus kodakarensis, Xanthomonas axonopodis, Xanthomonas campestris; Xylella fastidiosa* and *Yersinia pestis*.

In some embodiments, the truncated SecG is a *Bacillus clausii* SecG.

In some embodiments, the truncated SecG generally includes at least the minimum number of amino acid residues that allows it to facilitate, e.g., be part of the polypeptide secretion pathway, or functionally contribute, directly or indirectly, to the secretion of a desired polypeptide. In some embodiments, the truncated SecG includes at least 30, 31, 32, 33, 34, 35, 36, 37, 38 or 39 amino acids of a full-length SecG. In some embodiments, the full-length SecG is a wild-type SecG. In other embodiments, the full-length SecG is a variant SecG. In some embodiments, the truncated SecG comprises the first at least 30, 31, 32, 33, 34, 35, 36, 37, 38 or the first 39 amino acids of the N-terminal region of the full-length SecG.

In some embodiments, the truncated SecG includes at least one region or domain of a full-length, native or variant SecG. In some embodiments, the truncated SecG contains at least one transmembrane region. In some embodiments, the truncated SecG contains only one transmembrane region. In some embodiments, the transmembrane region corresponds to the N-terminal transmembrane segment of the full-length SecG.

In some embodiments, the truncated SecG may or may not interact with one or more "secretion-associated proteins." In some embodiments, the truncated SecG interacts with one or more secretion-associated proteins. In some embodiments, the truncated SecG does not interact with one or more secretion-associated proteins. The term "secretion-associated protein" as used herein generally refers to a protein involved in the secretion of a protein of interest from a host cell. The secretion-associated proteins may assist a nascent (i.e., during or immediately after synthesis) protein to fold correctly, in the movement of a protein from the intracellular to extracellular environment (e.g., moving through the cytoplasm to the cell membrane and/or across the membrane/cell wall to the extracellular milieu, etc.), appropriate processing and the like. Proteins involved in any aspect of the movement of a protein once it is synthesized intracellularly until it emerges on the external surface of the cell membrane are considered to have secretion-associated activity or function. Examples of such a protein include, but are not limited to, a protein involved in assisting the nascent protein of interest achieve a correctly folded conformation, or a protein from the Sec pathway. The terms "secretion-associated protein," "secretion-associated factor," and "secretion factor" are all used interchangeably herein.

In some embodiments, the invention provides a polynucleotide encoding a "hybrid" truncated SecG. The hybrid truncated SecG contains a region of more than one full-length SecGs. Such a hybrid truncated SecG contains a region from a first full-length SecG and a region from a second full-length SecG. The first or the second full-length SecG can be either a wild-type SecG or a variant SecG. In some embodiments, the first or the second full-length SecG is a bacterial, e.g., a *Bacillus* SecG.

In some embodiments, the truncated SecG is a hybrid truncated SecG containing two regions that include regions from the full-length SecGs of two different bacterial strains, a first strain and a second strain. In some embodiments, the first strain is *B. clausii* and the second strain is *B. subtilis*. In some embodiments, the first strain and the second strain include, but are not limited to *B. licheniformis* and *B. subtilis; Geobacillus stearothermophilus* and *B. subtilis; G stearothermophilus* and *B. licheniformis; B. clausii* and *B. licheniformis; B. lentus* and *B. subtilis; Escherichia coli* and *B. subtilis; B. amyloliquefaciens* and *B. subtilis; B. amyloliquefaciens* and *B. licheniformis*. In some embodiments, the N-terminal region of the hybrid truncated SecG contains a region from a *B. clausii* SecG and the C-terminal region of the hybrid truncated SecG contains a region from a *B. subtilis* SecG.

In general the truncated SecGs of the present teachings increase the production of the desired polypeptide as compared to the production of the desired polypeptide by a host bacterial cell that does not contain the truncated SecG. In some embodiments, the truncated SecG increases the production of the desired polypeptide by at least about 20%, about 30%, about 40%, about 50%, about 60%, about 70%, about 75% about 80%, about 85%, about 90%, about 95%, about 100%, about 125%, about 150%, about 175%, about 200% or about 250% as compared to the production of the desired polypeptide by a host bacterial cell that does not contain the truncated SecG. In some embodiments, the bacterial host cell containing the truncated SecG contains an endogenous SecG. In other embodiments, the endogenous SecG gene of the bacterial host cell is deleted. In other embodiments, the endogenous SecG gene of the bacterial host cell is replaced with a heterologous full-length SecG gene. In other embodiments, the endogenous SecG gene of the bacterial host cell is replaced with a heterologous truncated SecG gene.

In some embodiments, the truncated SecG contains a region from a wild-type or variant full-length SecG and increases the secretion of the desired polypeptide as compared to the secretion of the desired polypeptide by a host bacterial cell that contains the full-length SecG. In some embodiments, the truncated SecG increases the secretion of the desired polypeptide by at least about 20%, about 30%, about 40%, about 50%, about 60%, about 70%, about 75% about 80%, about 85%, about 90%, about 95%, about 100%, about 125%, about 150%, about 175%, about 200% or about 250% as compared to the secretion of the desired polypeptide by a host bacterial cell that contains the full-length SecG.

In some other aspects, the invention provides an expression vector, e.g., bacterial expression vector, and a host cell containing the polynucleotides described above and polypeptides encoded by the polynucleotides described above. Appropriate vectors, e.g., bacterial expression vectors with appropriate promoter(s), selection marker(s), etc are known to one of skill in the art. In some embodiments, the expression vector comprises the aprE promoter of the aprE gene from which the *B. subtilis* subtilisin is naturally transcribed. In some embodiments, the host cell comprises an aprE promoter that is the wild-type aprE promoter TGGGTCTACTAAAATATTAT-TCCATCTATTACAATAAATTCACAGA (SEQ ID NO:39; U.S. Patent Application Publication No. 20030148461). In other embodiments, the host cell comprises a mutant of the *B. subtilis* aprE promoters. In some embodiments, the invention provides for a *Bacillus* host cell that contains a mutant aprE promoter operably linked to a polynucleotide sequence that encodes a protein of interest. Thus, the invention encompasses host cells that express a protein of interest from a mutant aprE promoter. An example of a mutant aprE promoter is the mutant aprE promoter having the sequence

```
                                    (SEQ ID NO: 40)
TGGGTC TTGACA AATATTATTCCATCTAT TACAAT

AAATTCACAGA,
``` which is described in U.S. Patent Application Publication No. 20030148461.

In some embodiments, the bacterial host cell comprises a polynucleotide that encodes a heterologous SecG that is capable of facilitating the secretion of a desired protein by the host cell. In some embodiments, the host cell comprises a polynucleotide encoding a heterologous SecG that is capable of increasing the production of a desired protein when compared to the production of the same desired protein by a corresponding host cell, which does not express the heterologous SecG. In some embodiments, the heterologous SecG is a full-length SecG. In other embodiments, the heterologous SecG is a truncated SecG.

The host cell containing the polynucleotide of the present teachings can be any host cell in which the secretion of the desired polypeptide needs to be facilitated. In some embodiments, the host cell is a bacterial cell. In some embodiments, the host cell is a *Bacillus* or a *Geobacillus* cell. Examples of host cells include, but are not limited to *Acinetobacter, Agrobacterium tumefaciens, Azoarcus, Bacillus anthracis, Bacillus clausii, Bacillus licheniformis, Bacillus amyloliquefaciens, Bacillus subtilis, Bacillus lentus, Bacillus halodurans, Bifidobacterium longum, Buchnera aphidicola, Campestris, Campylobacter jejuni, Clostridium perfringens, Escherichia coli, Erwinia carotovora, Francisella tularensis, Haemophilus influenzae, Helicobacter pylori, Mycobacterium tuberculosis, Neisseria meningitides, Pseudomonas aeruginosa, Prochlorococcus marinus, Streptococcus pneumoniae, Salmonella enterica, Shewanella oneidensis, Salmonella enterica, Salmonella typhimurium, Staphylococcus epidermidis, Staphylococcus aureus, Shigella flexneri, Streptomyces coelicolor, Streptomyces lividans, Tropheryma whipplei, Tularensis, Temecula, Thermosynechococcus elongates, Thermococcus kodakarensis, Xanthomonas axonopodis, Xanthomonas campestris; Xylella fastidiosa* and *Yersinia pestis* host cells.

In some embodiments, the *Bacillus* strain of interest is an alkalophilic *Bacillus*. Numerous alkalophilic *Bacillus* strains are known (See e.g., U.S. Pat. No. 5,217,878; and Aunstrup et al., Proc IV IFS: Ferment. Tech. Today, 299-305 [1972]). Another type of *Bacillus* strain of particular interest is a cell of an industrial *Bacillus* strain. Examples of industrial *Bacillus* strains include, but are not limited to *B. licheniformis, B. lentus, B. subtilis, B. clausii*, and *B. amyloliquefaciens*. In additional embodiments, the *Bacillus* host strain is selected from the group consisting of *B. licheniformis, B subtilis, B. lentus, B. brevis, B. stearothermophilus, B. alkalophilus, B. amyloliquefaciens, B. coagulans, B. circulans, B. lautus, B. pumilus, B. thuringiensis*, and *B. megaterium* as well as other organisms within the genus *Bacillus*. In some embodiments, the host cell is a *Bacillus subtilis* cell.

In some embodiments, the industrial host strains are selected from the group consisting of non-recombinant strains of *Bacillus* sp., mutants of a naturally-occurring *Bacillus* strain, and recombinant *Bacillus* host strains. Preferably, the host strain is a recombinant host strain, wherein a polynucleotide encoding a polypeptide of interest has been previously introduced into the host. A further preferred host strain is a *Bacillus subtilis* host strain, and particularly a recombinant *Bacillus subtilis* host strain. Numerous *B. subtilis* strains are known and suitable for use in the present invention (See e.g., 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain; Hoch et al., Genetics, 73:215-228 [1973]; U.S. Pat. Nos. 4,450,235; 4,302,544; EP 0134048). The use of *B. subtilis* as an expression host is well known in the art (See Palva et al., Gene, 19:81-87 [1982]; Fahnestock and Fischer, J. Bacteriol., 165:796-804 [1986]; and Wang et al, Gene 69:39-47 [1988]).

Of particular interest as host cells are cells of industrial protease-producing Bacillus strains. By using these strains, the high efficiency of protease production is further enhanced by the use of heterologous SecG proteins provided by the present invention. Industrial protease producing *Bacillus* strains provide particularly preferred expression hosts. In some embodiments, use of these strains in the present invention provides further enhancements in protease production. As indicated above, there are two general types of proteases are typically secreted by *Bacillus* sp., namely neutral (or "metalloproteases") and alkaline (or "serine") proteases. In some embodiments, the proteases are *B. clausii* proteases e.g. the proteases of SEQ ID NOS: 25-29, 36 and 38. Other proteases include a wide variety of *Bacillus* subtilisins, which have been identified and sequenced, for example, subtilisin 168, subtilisin BPN', subtilisin Carlsberg, subtilisin DY, subtilisin 147, subtilisin 309 (See e.g., EP 414279 B; WO 89/06279; and Stahl et al., J. Bacteriol., 159:811-818 [1984]), *B. lentus* subtilisin, and *B. clausii* subtilisin, (J C van der Laan, G Gerritse, L J Mulleners, R A van der Hoek and W J Quax. Appl Environ Microbiol. 57: 901-909 [1991]).

In some embodiments of the present invention, the *Bacillus* host strains produce mutant (e.g., variant) proteases. Numerous references provide examples of variant proteases and reference (See e.g., WO 99/20770; WO 99/20726; WO 99/20769; WO 89/06279; RE 34,606; U.S. Pat. Nos. 4,914, 031; 4,980,288; 5,208,158; 5,310,675; 5,336,611; 5,399,283;. 5,441,882; 5,482,849; 5,631,217; 5,665,587; 5,700,676; 5,741,694; 5,858,757; 5,880,080; 6,197,567; and 6,218,165.

In some other embodiments, the invention provides for bacterial host cells in which the endogenous SecG gene is deleted, partially truncated, or mutated. In some embodiments, the present teachings provide a bacterial cell in which the SecG promoter contains one or more mutations. In some embodiments, the present teachings provide a bacterial cell in which the endogenous full-length SecG gene is deleted in its entirety, e.g., via recombination or any other means suitable for knock-out. In other embodiments, the endogenous gene of the host cell is complemented by the heterologous secG gene. In yet other embodiments, the endogenous gene of the host cell is replaced by the heterologous secG gene. In some other embodiments, the present teachings provide a bacterial cell in which the endogenous full-length SecG is partially truncated as described above about the truncated SecGs provided by the present teachings.

In some embodiments, the present teachings provide a bacterial cell in which the endogenous secG gene contains one or more mutations. Examples of these mutations include any mutation that introduces one or more stop codons within the coding region of a native, full-length secG gene, any mutation that modifies the structure of SecG protein, especially its structure conformation in the context of its interaction with cell membrane(s), any mutation that modifies SecG's function in association with sec related secretion pathway, any mutation that interferes with or modifies SecG's interaction with one or more components, e.g., secY, secA, secE, secF, secD, ftsY, SRP complex, proteins of the sec-dependent secretion pathway or machinery, any mutation that decreases the transcription or translation of endogenous secG gene, any mutation that directly or indirectly modifies post-transcription or post-translation process of secG protein so that modifies its function or activity, e.g., activity in polypeptide secretion.

In some embodiments, the present teachings provide a bacterial cell containing a compound or entity, e.g., antisense that decreases the transcription and/or translation of secG gene, or decreases the activity or function of SecG, e.g., activity or function in its interaction with cell membrane or in polypeptide secretion.

In some embodiments, the present teachings provide a bacterial cell in which a promoter contains one or more mutations, wherein relative amount of SecG is decreased as compared to wild type cells. Examples of these mutations include any mutation any mutation that inhibits or decreases the transcription or translation of endogenous secG gene.

In some embodiments, the present teachings provide a bacterial cell expressing a polynucleotide with one or more mutations as described above in the present teachings wherein the bacterial cell's endogenous secG is deleted partially or in its entirety.

Not wishing to be bound to any particular technical explanation, it is the discovery of the present teaching that a bacterial cell with decreased activity of SecG, e.g., truncated, mutated, deleted, etc. as described above is capable of providing the same or higher level of protein secretion as compared to a bacterial cell containing wild-type SecG.

In some embodiments, the bacterial cell of the present teachings secretes a desired polypeptide in an amount that is the same, or is increased, compared to a bacterial cell in which the endogenous secG gene has not been deleted, or in which the endogenous secG gene has not been replaced by a polynucleotide encoding a native, truncated SecG. In some embodiments, the secretion of the desired polypeptide is increased by at least 20 about 30%, about 40%, about 50%, about 60%, about 70%, about 75% about 80%, about 85%, about 90%, about 95%, about 100%, about 125%, about 150%, about 175%, about 200% or about 250% as compared to the secretion of the desired polypeptide by a bacterial cell that contains the full-length endogenous SecG. The bacterial cell of the present teachings can be any bacterial cell from which the desired polypeptide is to be secreted. In some embodiments, the bacterial cell is a *Bacillus* or a *Geobacillus* cell, as described above. In other embodiments, the bacterial cell is a *B. subtilis* cell.

The present teachings further provide a method of producing a desired polypeptide in a host cell. In some embodiments, the method comprises expressing the desired polypeptide and a heterologous SecG. In other embodiments, the method comprises expressing the desired polypeptide and a truncated heterologous SecG in the host cell. The host cells and the truncated SecG of the method are described above. In some embodiments, the host cell is cultured in a medium and the desired polypeptide is secreted into the medium. Appropriate media, culture conditions and methods of isolating the secreted desired polypeptide from the medium depends on several factors, including, but not limited to, the strain of the host cell, the nature of the desired polypeptide etc. The selection of an appropriate medium, culturing conditions and methods of isolation of the secreted desired polypeptide are known to one of skill in the art.

In some embodiments, the host cell further expresses endogenous SecG and the heterologous SecG is said to "complement" the endogenous SecG. In some embodiments, the host cell's (endogenous) SecG gene is replaced by the truncated SecG encoded by the polynucleotide described above.

In some embodiments, the desired polypeptide is from a first strain and the truncated SecG contains a region from a full-length SecG of the same strain. In some embodiments, the desired polypeptide and truncated SecG are from a strain of bacterial that is different from the host strain where secretion of the desired polypeptide takes place. In some embodiments, the desired polypeptide and truncated SecG are both from *B. clausii* and the host cell is *B. subtilis*.

The desired polypeptide can be any polypeptide that can be secreted by a host bacterial cell. In some embodiments, the desired polypeptide is a protease or an amylase. In some embodiments, the desired polypeptide is a protease from the Maxacal/GG36 family. In some embodiments, the desired polypeptide is an alkaline serine protease. In some embodiments, the desired polypeptide is an alkaline protease derived from an alkaliphilic *Bacillus*, such as *B. clausii* or *halodurans*, or from *B. lentus*. In some embodiments the desired protein is a variant of any of the alkaline proteases, more specifically a variant of alkaline serine proteases from *B. clausii* or *B. lentus*. In some embodiments the desired polypeptide is an amylase, variants of an amylase and, more generally any secreted enzyme.

In some embodiments, the present teachings also provide a method of producing a desired polypeptide in a bacterial cell. The method comprises expressing the desired polypeptide in a bacterial cell provided by the present teachings, e.g., a bacterial cell in which the endogenous secG gene has been deleted, mutated, truncated, etc. As described above, the desired polypeptide can be any polypeptide that can be secreted by a bacterial cell, e.g., a protease.

Aspects of the present teachings may be further understood in light of the following examples, which should not be construed as limiting the scope of the present teachings. It will be apparent to those skilled in the art that many modifications, both to materials and methods, may be practiced without departing from the present teachings.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: cpm (chloramphenicol); ppm (parts per million); M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml and mL (milliliters); μl and μL (microliters); cm (centimeters); mm (millimeters); μm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); $H_2O$ (water); $dH_2O$ (deionized water); (HCl (hydrochloric acid); aa (amino acid); bp (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); OD (optical density); Dulbecco's phosphate buffered solution (DPBS); $OD_{280}$ (optical density at 280 nm); $OD_{600}$ (optical density at 600 nm); $A_{405}$ (absorbance at 405 nm); PAGE (polyacrylamide gel electrophoresis); PBS (phosphate buffered saline [150 mM NaCl, 10 mM sodium phosphate buffer, pH 7.2]); PBST (PBS+0.25% TWEEN®-20); PEG (polyethylene glycol); PCR (polymerase chain reaction); SDS (sodium dodecyl sulfate); Tris (tris(hydroxymethyl)aminomethane); HEPES (N-[2-Hydroxyethyl]piperazine-N-[2-ethanesulfonic acid]); HBS (HEPES buffered saline); SDS (sodium dodecylsulfate); bME, BME and βME (beta-mercaptoethanol or 2-mercaptoethanol); Tris-HCl (tris[Hydroxymethyl]aminomethane-hydrochloride); Tricine (N-[tris-(hydroxymethyl)-methyl]-glycine); DMSO (dimethyl sulfoxide); Taq (Thermus aquaticus DNA polymerase); Klenow (DNA polymerase I large (Klenow) fragment); rpm (revolutions per minute); EGTA (ethylene glycol-bis(β-aminoethyl ether) N,N,N',N'-tetraacetic acid); EDTA (ethylenediaminetetracetic acid); bla (β-lactamase or ampicillin-resistance gene); DNA2.0 (DNA2.0, Menlo Park, Calif.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Pisacataway, N.J.); NCBI (National Center for Biotechnology Information).

EXAMPLE 1

Effect of Expression of *B. clausii* Full-Length SecG on the Production of Properase in a *B. subtilis* Host Cell This experiment was performed to test whether expressing *B. clausii* SecG in *B. subtilis* would improve the secretion of *B. clausii* proteins by *B. subtilis* host cells.

This example describes the experiments performed to determine the effect of expressing the heterologous *B. clausii* secG gene on the production of the *B. clausii* serine protease Properase (SEQ ID NO:29) by a *B. subtilis* host cell in which the gene encoding the *B. clausii* complements the expression of the endogenous *B. subtilis* SecG.

For integration into the *B. subtilis* chromosome, the *B. clausii* SecG ($SecG^C$) was assembled in a fusion between the upstream and downstream regions of the *B. subtilis* SecG ($SecG^S$). First, 1000 base pairs of the region upstream of $SecG^S$ were amplified via PCR from chromosomal DNA from *B. subtilis* strain BG2942. The following primers were used to amplify the region while adding an AvaI restriction site to the 5' end and an overhang for PCR fusion to the 3' end.
JS#56: F AvaI-1 kb up SecG$^S$ (SEQ ID NO: 13)
GGCGCGCCCGGGGAGGATCTTTTTTACTATGATTTCG JS#53: R *B. subtilis* 1 kb up/SecG$^C$ Fusion (SEQ ID NO: 14)
TGCGATCATCAAAAACAGCTGCATCCCATACACCTCCAGACTCA Similarly, 1000 base pairs of the region downstream of SecG$^C$ were amplified from chromosomal DNA via PCR to incorporate a 5' overhang for PCR fusion and a 3' SacI restriction site.
JS#54: F SecG$^C$/*B. subtilis* 1 kb Down Fusion (SEQ ID NO: 15)
GGGTTAAATGCGTATTTCCTATAAGGCGGCAATGTTTGTATAA JS#17: R SacI-1 kb Down SecG$^S$ (SEQ ID NO: 16)
GCGCGGAGCTCGCTTCCGTAATATTTAACATCTCC The *B. clausii* secG was amplified via PCR from chromosomal DNA from *B. clausii* strain PB92. The following primers incorporate both 5' and 3' overhangs for fusion PCR.
JS#52: F *B. subtilis* 1 kb up/SecG$^C$ fusion (SEQ ID NO: 17)
TGAGTCTGGAGGTGTATGGGATGCAGCTGTTTTTGATGATCGCA JS#55: R SecG$^C$/*B. subtilis* 1 kb Down Fusion (SEQ ID NO: 18)
TTATACAAACATTGCCGCCTTATAGGAAATACGCATTTAACCC The *B. subtilis* upstream PCR fragment was then fused via PCR to the *B. clausii* secG with primers JS#56 and JS#55. Lastly, this upstream-secG PCR fragment was fused via PCR to the *B. subtilis* downstream PCR fragment with primers JS#56 and JS#17. The final fusion product is upstream-secG$^C$-downstream.

This secG$^C$ fusion product was digested with AvaI and SacI and ligated in the vector pUC19spcR also digested with AvaI and SacI. The ligation mixture underwent rolling circle amplification (RCA) and the RCA product was transformed into BG2942, selecting on 100 ug/ml spectinomycin. The secG$^C$ and plasmid DNA were integrated at the *B. subtilis* secG locus via a single cross over. This strain was named JS1003. JS1003 was transformed with chromosomal DNA from the Properase expressing strain GICC3147, and the transformants were selected on 100 ug/ml spectinomycin and 5 ug/ml chloramphenicol. This strain was amplified to 25 ug/ml chloramphenicol and was named JS1015. GICC3147 is a strain derived from BGSEC94, and contains the gene encoding a Properase that carries mutations W7G and E57G.

A control strain was generated by transforming BG2942 with chromosomal DNA from GICC3147. Transformants were selected on 5 ug/ml chloramphenicol and the strain was further amplified to 25 ug/ml chloramphenicol. This control strain was named JS1009.

The level of Properase secreted by the JS1015 and the JS1009 strains was determined by assaying the secreted proteases for activity against the substrate, succinyl-L-Ala-L-Ala-L-Pro-L-Phe-p-nitroanalide (AAPF). The assay measured the production of modified protease as the increase in absorbance at 405 nm/min resulting from the hydrolysis and release of p-nitroanaline (Estell et al., J Biol Chem., 260: 6518-6521 (1985)). The measurements were made using the Sofmax Pro software, and the specified conditions were set as: Type: Kinetic; Reduction: Vmax Points (Read best 15/28 points); Lm1: 405 nm; Time: 5 minutes; and Interval: 11 Seconds. Ten microliters of each of the *B. subtilis* cultures were diluted 100 ul of Tris Buffer, containing 10 mM Tris+ 0.005% TWEEN®-80, pH 8.6; and 25 ul of 100 mg/ml AAPF. The relative activity of each of the *B. clausii* proteases was calculated, and the effect of SecG on the production of the *B. clausii* protease was determined as the activity of the secreted protease.

Figure 2:
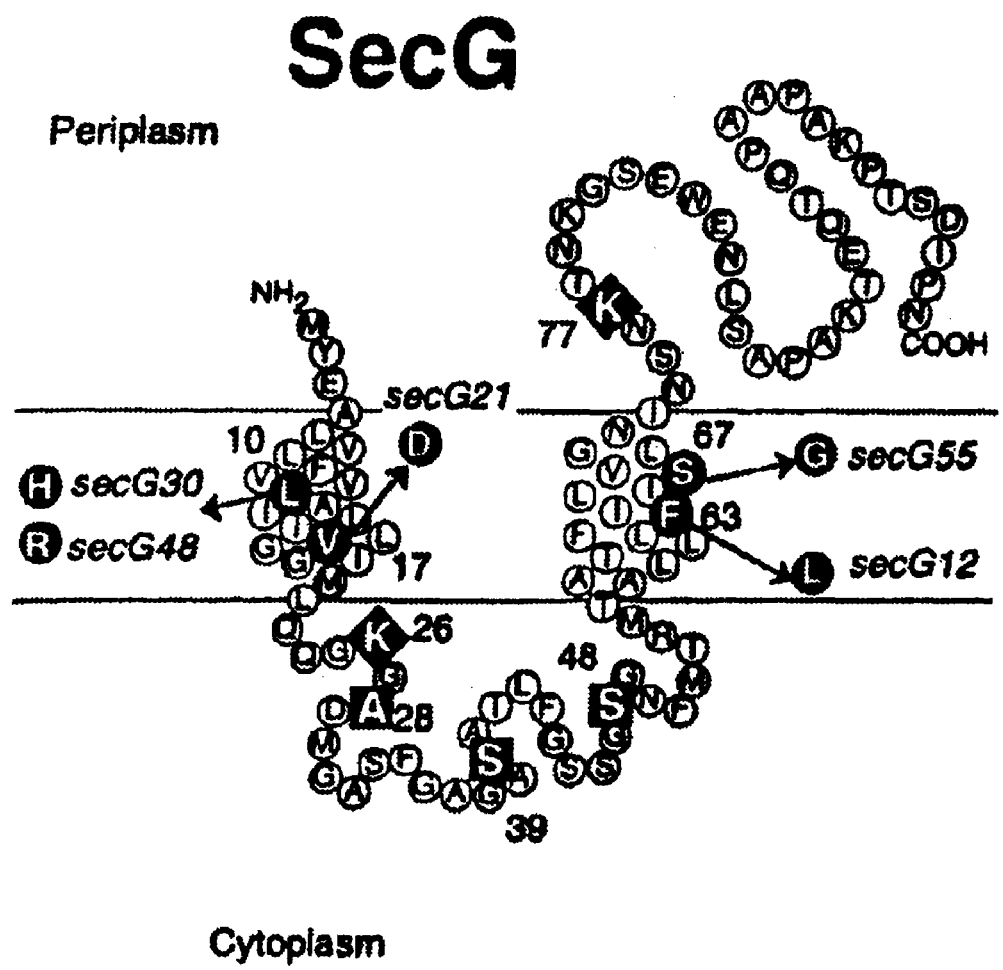
FIG. 2 shows a topology model of an *E. coli* SecG [(Satoh et al. Biochemistry 42:7434-7441 (2003)].

The results are provided in FIG. 1, and they show that expressing the full-length *B. clausii* SecG in a *B. subtilis* host cell by complementing the *B. subtilis* host cell's endogenous secG gene with the *B. clausii* secG gene (strain JS1015) surprisingly resulted in a much greater production of Properase when compared to the production of Propearase by the control JS1009 *B. subtilis* host cell, which does not contain the *B. clausii* secG gene. Sequencing of the *B. clausii* secG gene that had been introduced into the *B. subtilis* chromosome revealed that I contained a stop codon corresponding to position 40 of the otherwise full-length SecG protein (SEQ ID NO:9), thus encoding a truncated SecG that contained the first N-terminal 39 amino acids of the full-length 77 amino acid SecG protein (SEQ ID NO:11). According to the topology of SecG proteins e.g. as shown in FIG. 2, the truncated SecG encompasses only one transmembrane domain.

Therefore, the data indicate that expressing a truncated heterologous SecG in a host cell that expresses a protein of interest e.g. a protease, results in an increase in the production of the protein of interest by the host cell that expresses the heterologous truncated SecG.

The effect of the truncated SecG (SEQ ID NO:11) and of the full-length SecG (SEQ ID NO:9) on the production of other proteases by *B. subtilis* host cells was determined as described below.

EXAMPLE 2

Construction of Exemplary Host Strains

This example describes methods that were used to generate bacterial host strains in which the endogenous secG gene was maintained or deleted, replaced by either a full-length or a truncated heterologous secG gene, or complemented by either full-length or a truncated heterologous secG gene.

Three sets of *B. subtilis* host strains were generated as summarized in Table 1, and as described below.

TABLE 1

| *B.subtilis* strains | |
|---|---|
| Strain Name | Description - *B. subtilis* cell comprising: |
| SET A | |
| CF368 | SecG truncated (stop codon @ 40) complementing endogenous SecG |
| CF369 | SecG truncated (stop codon @ 40) replacing endogenous SecG |

TABLE 1-continued

B. subtilis strains

| Strain Name | Description - B. subtilis cell comprising: |
|---|---|
| CF370 | SecG full-length replacing endogenous SecG |
| CF385 | Endogenous SecG deleted |
| SET B | |
| CF363 | V049 (AA SEQ ID NO: 26: PNT SEQ ID NO: 31) |
| CF365 | V049-E33Q (AA SEQ ID NO: 27: PNT SEQ ID NO: 32) |
| CF366 | V049-E33R (AA SEQ ID NO: 28: PNT SEQ ID NO: 33) |
| CF381 | Properase (AA SEQ ID NO: 29: PNT SEQ ID NO: 34) |
| SET C | |
| CF371: 368 × 363 | SecG truncated/complement/V049 |
| CF372: 365 × 368 | SecG truncated/complement/V049-E33Q |
| CF373: 366 × 368 | SecG truncated/complement/V049-E33R |
| CF374: 368 × 381 | SecG truncated/complement/Properase |
| CF375: 369 × 363 | SecG truncated/replacement/V049 |
| CF376: 365 × 369 | SecGSecG truncated/replacement/V049-E33Q |
| CF377: 366 × 369 | SecG truncated/replacement/V049-E33R |
| CF378: 369 × 381 | SecG truncated/replacement/Properase |
| CF379: 370 × 363 | SecG full-length/replacement/V049 |
| CF380: 370 × 381 | SecG full-length/replacement/Properase |
| CF396: 395 × 363 | Endogenous SecG deleted/Properase |

*SecG truncated was derived from the full-length B. clausii SecG (SEQ ID NO: 9), and it has an amino acid sequence of SEQ ID NO: 11 encoded by a polynucleotide sequence of SEQ ID NO: 12.

Chromosomal DNA was extracted from each of the B. subtilis cells of strains of SET A and transformed into the B. subtilis cells of the strains of SET B to generate the B. subtilis strains of SET C according to the crosses indicated in Table 1.

I. Construction of A strains (1) Construction of the B. subtilis Host Strains Containing an Integrating Plasmid Expressing the Polynucleotide Encoding a Truncated B. clausii SecG to Complement the Expression of the B. subtilis SecG (strain CF368) Set A A fragment of DNA was amplified from a Bacillus subtilis publicly available wild type lab strain known as I168 that contained a 1 Kb fragment of the area just upstream of the B. subtilis SecG gene using the following primers:

JS 56 (Forward) Start of B. subtilis SecG upstream area AvaI:

```
                                          (SEQ ID: 13)
GGCGCGCCCGGGGAGGATCTTTTTTACTATGATTTCG
```

JS 53 (Reverse) End of B. subtilis SecG upstream (fusion to B. clausii SecG 5'):

```
                                          (SEQ ID NO: 14)
TGCGATCATCAAAAACAGCTGCATCCCATACACCTCCAGACTCA
```

The Bacillus clausii secG gene was amplified from a strain known as PB 92 (U.S. Pat. No. 7,247,450) using the following primers:

JS 52 (Forward) Start of B. clausii SecG (fusion to B. subtilis SecG upstream):

```
                                          (SEQ ID NO: 17)
TGAGTCTGGAGGTGTATGGGATGCAGCTGTTTTTGATGATCGCA
```

JS 55 (Reverse) End of B. clausii SecG (fusion to B. subtilis SecG downstream):

```
                                          (SEQ ID NO: 18)
TTATACAAACATTGCCGCCTTATAGGAAATACGCATTTAACCC
```

Another fragment containing 1 Kb of the area just downstream of the B. subtilis SecG was amplified from the same PCR fragment using the following primers:

JS 54 (Forward) Start of B. subtilis SecG downstream (fusion primer to end of B. clausii secG gene):

```
                                          (SEQ ID NO: 15)
GGGTTAAATGCGTATTTCCTATAAGGCGGCAATGTTTGTATAA
```

JS 17 (Reverse) End of B. subtilis SecG downstream SacI:

```
                                          (SEQ ID NO: 16)
GCGCGGAGCTCGCTTCCGTAATATTTAACATCTCC
```

The pieces were fused together using PCR with the following primers:

JS 56 (Forward) Start of B. subtilis SecG upstream area AvaI:

```
                                          (SEQ ID NO: 13)
GGCGCGCCCGGGGAGGATCTTTTTTACTATGATTTCG
```

JS 17 (Reverse) End of B. sub SecG downstream SacI:

```
                                          (SEQ ID NO16)
GCGCGGAGCTCGCTTCCGTAATATTTAACATCTCC
```

The resulting piece was digested AvaI/SacI and ligated into the well described vector pUC19, which was also digested AvaI/SacI. The vector had been previously modified by ligating the spectinomycin resistance gene into the BamHI site.

The resulting plasmid, known as pJS3, was transformed into a Bacillus subtilis lab strain known as BG 2942 (ΔnprE, degUHy32), which had previously been made competent. The plasmid integrated into the B. subtilis SecG locus with a single cross-over event, thus leaving the B. subtilis SecG intact. The resulting strain was selected on LA+100 µg/mL spectinomycin. A transformant was selected and struck out onto LA+100 µg/mL spectinomycin and a single colony was chosen and grown in LB+µg/mL spectinomycin until an OD 600 of 1 was reached, and then frozen glycerol stocks were made and stored at −80° C. This strain is known as JS 1003.

(2) Construction of the Bacillus subtilis Host Where the B. clausii Truncated SecG Replaces the B. subtilis (full length) SecG (CF369) SET A A 1 Kb piece upstream of the Bacillus subtilis secG gene containing the secG promoter was amplified from a Bacillus subtilis strain known as JS 1003 (see above description) with the following primers:

JS 56 (Forward) Start of B. subtilis SecG Upstream area:

```
                                          (SEQ ID NO: 13)
GGCGCGCCCGGGGAGGATCTTTTTTACTATGATTTCG
```

JS 53 (Reverse) End of B. subtilis SecG upstream (fusion primer to B. clausii SecG):

```
                                          (SEQ ID NO: 14)
TGCGATCATCAAAAACAGCTGCATCCCATACACCTCCAGACTCA
```

The Bacillus clausii secG gene was amplified from a strain known as JS 1003 with the following primers:

JS 52 (Forward) Start of B. clausii secG gene Fusion primer to b. sub SecG upstream):

(SEQ ID NO: 17)
TGAGTCTGGAGGTGTATGGGATGCAGCTGTTTTTGATGATCGCA

JS 68 (Reverse) End of B. clausii SecG (fusion primer to lox spec):

(SEQ ID NO: 19)
GGATCCAGCTTATCGATACCGTCGATTATAGGAAATACGCATTTAACCCT

The spectinomycin resistance gene flanked by the lox sites was amplified from a plasmid that had previously been sequenced with the following primers:

JS 67 (Forward) Start of lox-spec-lox (fusion primer to end B. clausii SecG):

(SEQ ID NO: 20)
AGGGTTAAATGCGTATTTCCTATAATCGACGGTATCGATAAGCTGGATCC

JS 70 (Reverse) End of lox-spec-lox (fusion primer to B. subtilis SecG downstream:

(SEQ ID NO: 21)
CATCAGACCTTATACAAACATTGCCGGCCTAGGATGCATATGGCGGCCGC

A 1 Kb piece just downstream of the Bacillus subtilis secG gene containing the terminator was amplified from a strain known as JS 1003 with the following primers:

JS 69 (Forward) Start of B. subtilis SecG downstream (fusion to lox-spec-lox):

(SEQ ID NO: 22)
GCGGCCGCCATATGCATCCTAGGCCGGCAATGTTTGTATAAGGTCTGATG

JS 17 (Reverse) End of B. subtilis SecG downstream area:

(SEQ ID NO: 17)
GCGCGGAGCTCGCTTCCGTAATATTTAACATCTCC

The pieces were fused together using fusion PCR (Ho et al, 1989) with the following primers:

JS 56/JS 53 piece was fused to JS 52/JS68 with primers JS 56 and JS 68.

JS 67/JS 70 was fused to JS 69/JS 17 with primers JS 67 and JS 17.

The above pieces were fused together with primers JS 56 and JS 17.

Figure 8:
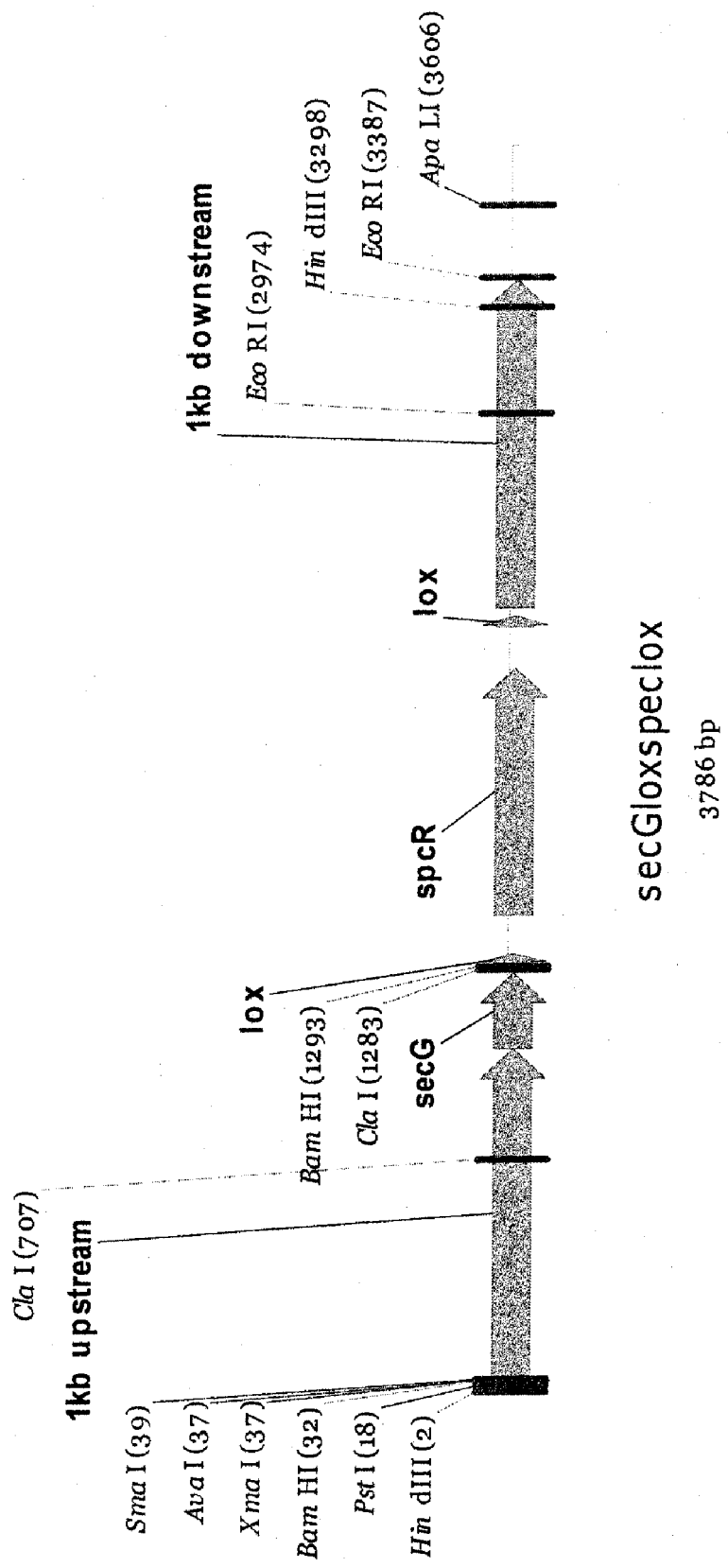
FIG. 8 shows a map of the construct that was transformed into *B. subtillis* to replace the endogeneous *B. subtilis* secG gene with the secG gene from *B. clausii*.

The resulting PCR fusion, depicted in FIG. 8, shows the B. clausii truncated SecG that is now under the B. subtilis secG promoter, which is contained in the 1 Kb upstream piece.

This PCR fragment was transformed directly into a B. subtilis host, through a double-crossover event, it integrated into the secG locus and replaced the existing B. subtilis secG gene. A PCR fragment was generated from a colony of the strain and sequenced. Sequencing showed a stop codon at position 40, which was made by a CAG being mutated into a TAG.

(3) Construction of the Bacillus subtilis Host Where the Full-Length B. clausii SecG Replaces the B. subtilis (full length) SecG (CF370) SET A The CF370 strain was generated according to the method described for generating CF369 with the exception that the polynucleotide sequence that encodes the full-length SecG of B. clausii was used as the template for amplifying the full-length SecG.

(4) Construction of a Bacillus subtilis Host Strain Where the SecG Gene is Deleted (CF395) SET A A 1 Kb piece upstream of the Bacillus subtilis secG gene containing the secG promoter was amplified from a Bacillus subtilis strain known as JS 1003 (see above description) with the following primers:

JS 56 (Forward) Start of B. subtilis SecG Upstream area:

(SEQ ID NO: 13)
GGCGCGCCCGGGGAGGATCTTTTTTACTATGATTTCG

CF 07-17 (Reverse) End of B. subtilis SecG upstream (fusion to lox-spec-lox):

(SEQ ID NO: 23)
CAGCTTATCGATACCGTCGACCCATACACCTCCAGACTCAC

The spectinomycin resistance gene flanked by the lox sites fused to the B. subtilis SecG downstream piece was amplified from a previously described strain known as CF 375 with the following primers:

CF 07-16 (Forward) Fusion of SecG Upstream 3' to lox-spec-lox:

(SEQ ID NO: 24)
GTGAGTCTGGAGGTGTATGGGTCGACGGTATCGATAAGCTG

JS 17 (Reverse) End of B. sub SecG Downstream Area:

(SEQ ID NO: 16)
GCGCGGAGCTCGCTTCCGTAATATTTAACATCTCC

The pieces were fused together using fusion PCR (Ho et al, 1989) with the following primers:

JS 56 (Forward) Start of B. subtilis SecG Upstream area:

(SEQ ID NO: 13)
GGCGCGCCCGGGGAGGATCTTTTTTACTATGATTTCG

JS 17 (Reverse) End of B. sub SecG Downstream Area:

(SEQ ID NO: 16)
GCGCGGAGCTCGCTTCCGTAATATTTAACATCTCC

This PCR fragment was transformed directly into a B. subtilis host strain known as BGSEC94 (degU(Hy), oppA-) where, through a double-crossover event, it integrated into the SecG locus and replaced the existing B. subtilis secG gene.

This host was made competent and was transformed with chromosomal DNA from several B. subtilis strains expressing V049 (Puramax), V049 with the E33Q or E33R mutation, or Properase, integrated under the aprE promoter.

II. Construction of Set B Strains: Strains Expressing One of Alkaline Proteases V049, V049 -E33Q, V049-E33R, or Properase B. subtilis strains CF363, CF365, CF366 and CF381 were generated by transforming a B. subtilis known as BGSEC94 with an integrating vector containing the expression cassette comprising the B. subtilis alkaline protease (aprE) gene promoter, the first 8 codons of the B. subtilis aprE signal peptide fused to the ninth codon of the B. clausii alkaline serine protease signal peptide, and the gene encoding one of V049

(wt pro sequence), (amino acid sequence SEQ ID NO:26: polynucleotide sequence SEQ ID NO:31), V049-E33Q (pro sequence mutation) (amino acid sequence SEQ ID NO:27; polynucleotide sequence SEQ ID NO:32), V049-E33R (pro sequence mutation) (AA SEQ ID NO:28; polynucleotide sequence SEQ ID NO:33), and Properase (amino acid sequence SEQ ID NO:29; PNT SEQ ID NO:34).

The expression cassette along with the chloramphenicol acetyl transferase (catH, CAT) was digested out of the plasmid as a NotI fragment and ligated to itself forming the non-replicating V049-catH DNA circle. A Rolling Circle Amplification (TempliPhi™ DNA Amplification Kit, Amersham) was performed on the ligation mixture. To enhance the transformation frequency the rolling circle amplification was first used to transform the highly transformation competent strain BGSEC94 comK was transformed. The transformation was plated on Luria agar (LA)+5 µg/ml chloramphenicol with 1.6% skim milk plate and the best clearing transformant was chosen and streaked to single colonies on a LA+5 µg/ml cmp with 1.6% skim milk plate. One single colony was chosen and grown overnight in Luria broth (LB)+5 µg/ml cmp. This intermediate strain contains the correct protease—CAT expression cassette integrated into the chromosomal aprE locus. From this single culture, chromosomal DNA was extracted. This DNA was transformed to the *Bacillus subtilis* strain BGSEC94. The transformation was plated on LA+5 µg/ml cmp with 1.6% skim milk and the strain was further amplified on 25 µg/ml cmp. Frozen glycerol stocks were made. This procedure was repeated for each of V049, V049 E33Q/R, and Properase.

A loop of the vial was streaked onto a plate with LA+25 ug/ml cmp. One single colony was chosen and grown overnight in Luria broth (LB)+5 µg/ml cmp. From this single culture, chromosomal DNA was extracted. This DNA was transformed into the SecG host strains described above.

III. Construction of Set C Strains (Where Set A Strains are Crossed With Set B Strains)

See table above: The chromosomal DNA from each of the strains of SET B was transformed into the various SecG strains in Set A as described in Table 1. Selection was done on 100 ug/mL spectinomycin and 5 ug/mL cmp. Strains were amplified to 25 ug/mL cmp and glycerol vials were made of each strain and frozen at −80 C.

EXAMPLE 3

SecG and the Production of Protease V049 (SEQ ID NO:26) and Properase (SEQ ID NO:29)

This example describes experiments that were performed to determine the effect of expressing full-length (SEQ ID NO:9) or truncated SecG (SEQ ID NO:11) from *B. clausii* on the production of proteases V049 (SEQ ID NO:26) and Properase. (SEQ ID NO:29).

Shake Flask Experimental Data #1:

Strains CF363, CF371, CF375 and CF379 were isolated on LB plates containing 25 ug/mL chloramphenical (cmp) (to amplify the protease gene) and grown in shake flasks using FNII modified shake flask media. A 0.01% inoculum was used. Samples were taken at 24, 41, and 48 hours and the production of protease was determined as described in Example 1. The relative activity of each of the *B. clausii* proteases was calculated, and the effect of SecG on the production of the *B. clausii* protease was determined as the activity of the secreted protease.

Figure 3:
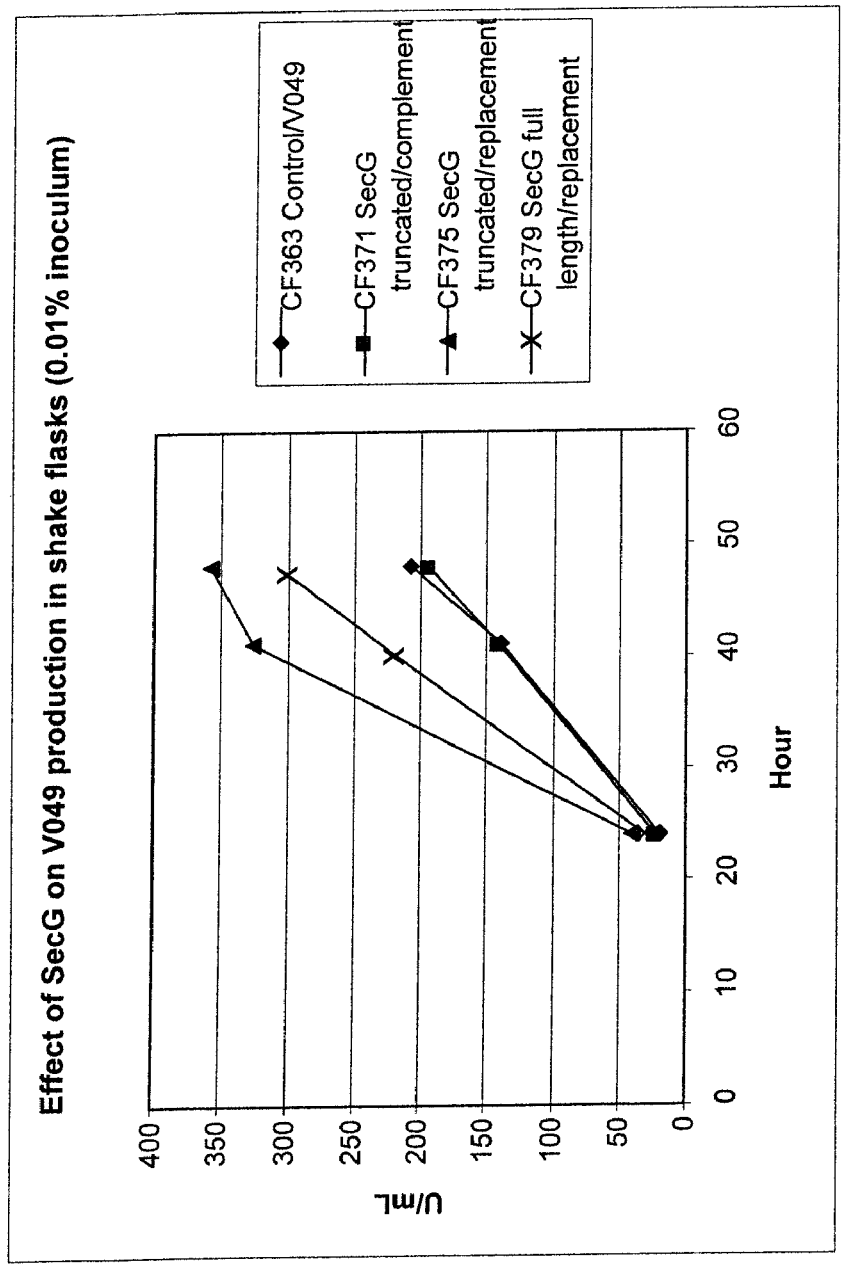
FIG. 3 shows the effect of truncated SecG from *B. clausii* (SEQ ID NO:11) on the production of the protease V049 (also known as Puramax; SEQ ID NO:26) by *B. subtilis* host cells in which the truncated *B. clausii* secG gene replaces (CF375) or is complement (CF371) to the endogeneous *B. subtitlis* gene; and the effect of full-length *B. clausii* SecG (SEQ ID NO:10) on the production of the protease V049 by *B. subtilis* host cells in which the full-length *B. clausii* secG gene replaces (CF379) the endogeneous *B. subtitlis* secG gene, when compared to the production of V049 by *B. subtilis* host cells expressing V049, which do not comprise either the truncated or full-length *B. clausii* secG gene (CF363). Growth of the cells was initiated using a 0.01% (v/v) inoculum.

The results of the effect of the expression of truncated SecG expressed in complement (CF371) or expressed and replacing the endogenous SecG (CF375), and the effect of expressing a full-length SecG while replacing the endogenous SecG on the production of protease V049 are shown in FIG. 3. These data were compared to the production of V049 by the control strain CF363.

These data show that a significant increase in production of V049 was attained by *B. subtilis* cells in which the endogenous secG was replaced with a truncated *B. clausii* secG. *B. subtilis* cells in which the endogenous secG gene was replaced with a full-length *B. clausii* secG gene also showed increase V049 production when compared to the production by the control strain CF363.

In a similar manner, the effect of SecG was tested on the production of Properase by strains CF381, CF374, CF 378 and CF380.

Figure 4:
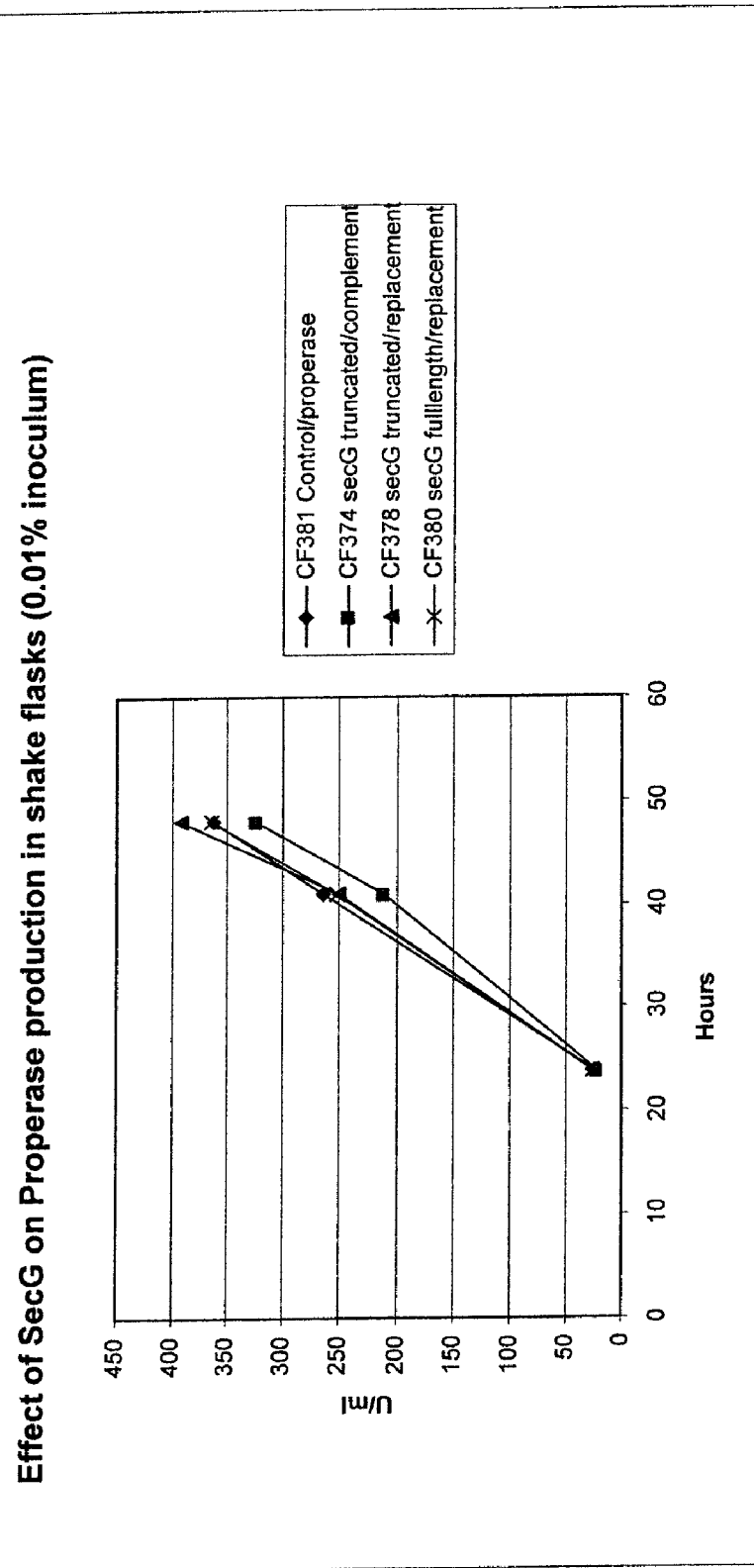
FIG. 4 shows the effect of expressing truncated SecG from *B. clausii* (SEQ ID NO:12) on the production of the protease Properase (SEQ ID NO:29) by *B. subtilis* host cells in which the truncated *B. clausii* secG gene replaces (CF378) or is complement (CF374) to the endogeneous *B. subtilis* gene; and the effect of full-length *B. clausii* SecG (SEQ ID NO:10) on the production of the protease Properase by *B. subtilis* host cells in which the full-length *B. clausii* secG gene replaces (CF380) the endogeneous *B. subtilis* secG gene, when compared to the production of Properase by *B. subtilis* host cells expressing Properase, which do not comprise either the truncated or full-length *B. clausii* secG gene (CF381). Growth of the cells was initiated using a 0.01% (v/v) inoculum.

The results are shown in FIG. 4. The data show that *B. subtilis* cells in which the endogenous secG was replaced with a truncated *B. clausii* SecG (strain CF378) produced greater levels of Properase than cells in which the endogenous secG was complemented with a truncated *B. clausii* SecG (CF374); greater than the cells in which the endogenous secG was replaced with a full-length *B. calusii* SecG; and greater than the CF381 control strain (FIG. 4).

Figure 5:
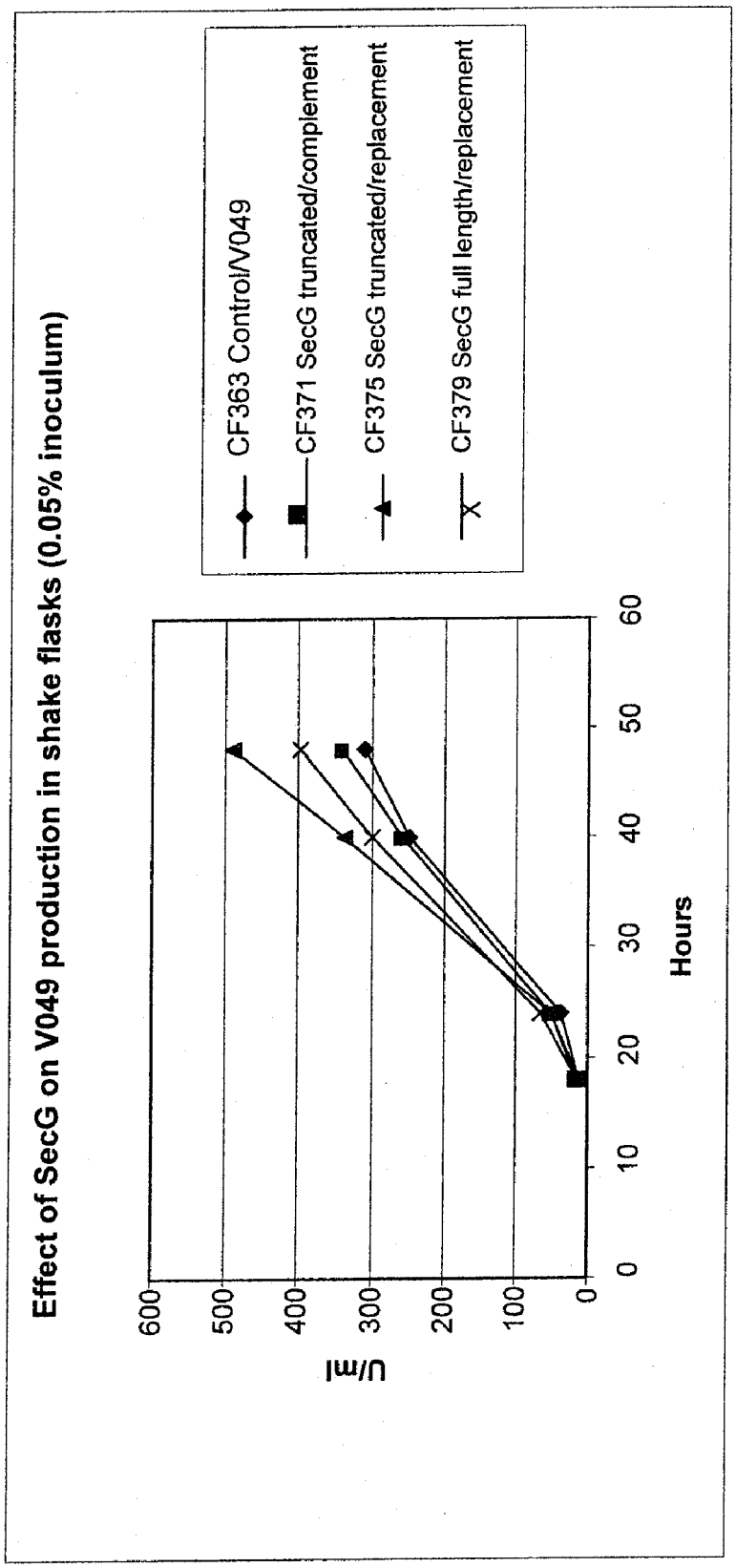
FIG. 5 shows the effects described in FIG. 3 when growth of the cells was initiated with a 5% inoculum.

Shake Flask Experimental Data #2:

The shake flask experiment described above was repeated with the same strains and using a 5% inoculum. Protease activity was measured in samples taken at 18, 24, 40, and 48 hours. The results of the second shake flask experiment with V049 being expressed in the SecG strains CF371, CF375 and CF389 are shown in FIG. 5. Strain CF375, in which the endogenous secG gene was replaced with the gene encoding the truncated *B. clausii* SecG (SEQ ID NO:11) again produced the greatest level of protease when compared to strains CF371 and CF379, and the CF363 control strain.

EXAMPLE 4

SecG and the Production of Protease Variants V049-E33Q (SEQ ID NO:27) and V049-E33R (SEQ ID NO:28)

Strains producing proteases V049-E33Q (SEQ ID NO:36), and V049-E33R (SEQ ID NO:28), and their relative controls (CF363) and were isolated on LB plates containing 25 ug/mL cmp (to amplify the protease gene) and grown in shake flasks using FNII modified shake flask media as described above. A 5% inoculum was used. Samples were taken at 24, 41, and 48 hours and the production of protease was determined by assaying the secreted proteases for activity against the substrate, succinyl-L-Ala-L-Ala-L-Pro-L-Phe-p-nitroanalide (AAPF).

Figure 6:
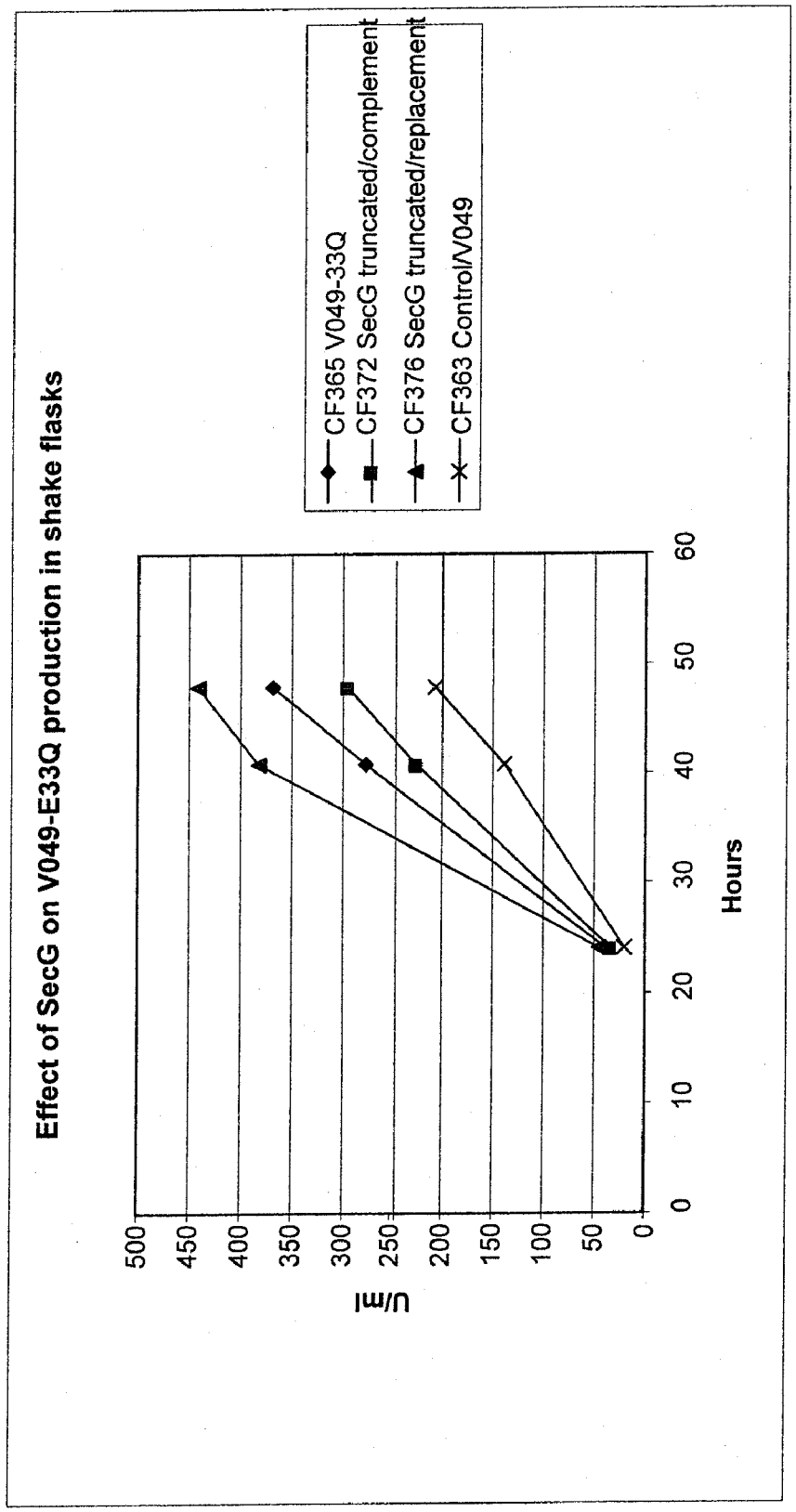
FIG. 6 shows the effect of truncated SecG from *B. clausii* (SEQ ID NO:11) on the production of the mutated protease V049-E33Q by *B. subtilis* host cells in which the truncated *B. clausii* secG gene replaces (CF376) or is complement (CF372) to the endogeneous *B. subtilis* gene when compared to the production of V049-E33Q by *B. subtilis* host cells expressing V049-E33Q (CF365) and V049 (CF363), which do not comprise the truncated *B. clausii* secG gene.

The data showing the effect of SecG on the production of variant V049-E33Q (SEQ ID NO:27) are shown in FIG. 6. The data show that *B. subtilis* cells in which the endogenous SecG was replaced with a truncated *B. clausii* SecG (strain CF376) produced greater levels of V049-E33Q than cells in which the endogenous SecG was complemented with a truncated *B. clausii* SecG (CF372); and greater than the production of V049-E33Q by the CF365 and CF363 control strain (FIG. 6).

Figure 7:
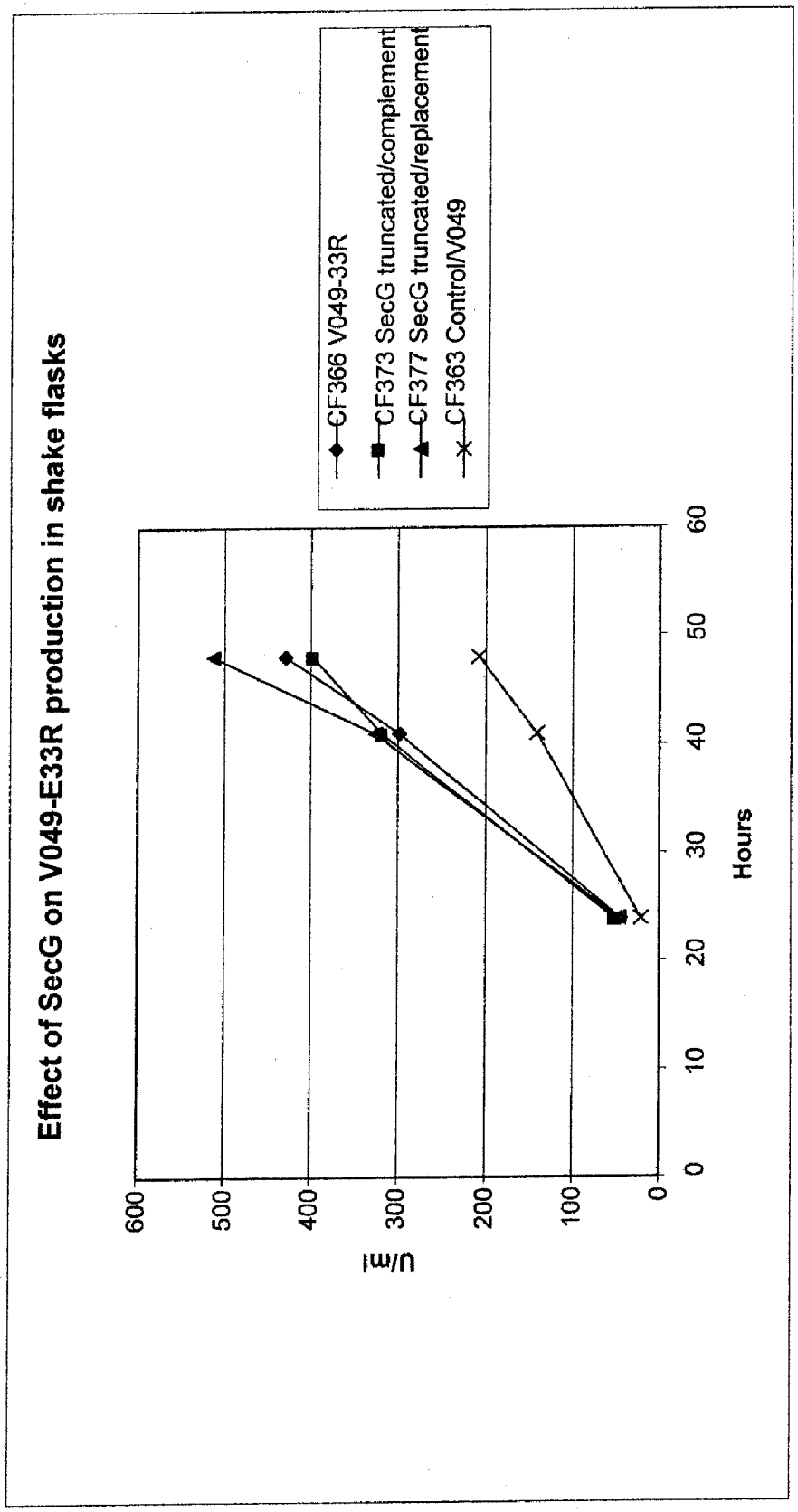
FIG. 7 shows the effect of truncated SecG from *B. clausii* (SEQ ID NO:11) on the production of the mutated protease V049-E33R by *B. subtilis* host cells in which the truncated *B. clausii* secG gene replaces (CF377) or is complement (CF373) to the endogeneous *B. subtilis* gene when compared to the production of V049-E33R by *B. subtilis* host cells expressing V049-E33R (CF366) and V049 (CF363), which do not comprise the truncated *B. clausii* secG gene.

The data showing the effect of SecG on the production of variant V049-E33R (SEQ ID NO:228) are shown in FIG. 7. The data show that *B. subtilis* cells in which the endogenous secG gene was replaced with a truncated *B. clausii* secG gene (strain CF377) produced greater levels of V049-E33R than cells in which the endogenous SecG was complemented with a truncated *B. clausii* SecG (CF373); and greater than the production of V049-E33R by the CF366 and CF363 control strain (FIG. 7).

Taken together, these data indicate that the expression of a truncated SecG in both a wild-type and a variant protease thereof, i.e. V049 and variants V049-E33Q and V049-E33R leads to the greatest increase in the production of each protease when compared to to the production of the proteases by the corresponding control strains, which do not express the truncated SecG.

EXAMPLE 5

Deletion of secG in a *Bacillus subtilis* Strain Expressing V049

A *Bacillus subtilis* strain was made where the secG gene was deleted altogether (CF395) (see Example 2). Chromosomal DNA from a Bacillus subtilis strain expressing the *B. clausii* alkaline serine protease variant known as V049 or Puramax (CF363) (see Example 2) was transformed into the host strain CF395 to form the strain CF396. CF363 and CF396 were grown in shake flasks using this protocol:

5 ml of LB+25 µg/ml cmp was inoculated with a single colony from an LA+25 ug/ml cmp plate and grown to an OD$_{600}$ of 1.0 and then 1 ml of this culture was inoculated into a shake flask containing 25 ml of FNII Modified Shake Flask Media. The shake flasks were grown at 37 C, 250 rpm for 48 hours and samples were removed at the 18, 24, 41, and 48 hour time-points.

Figure 9:
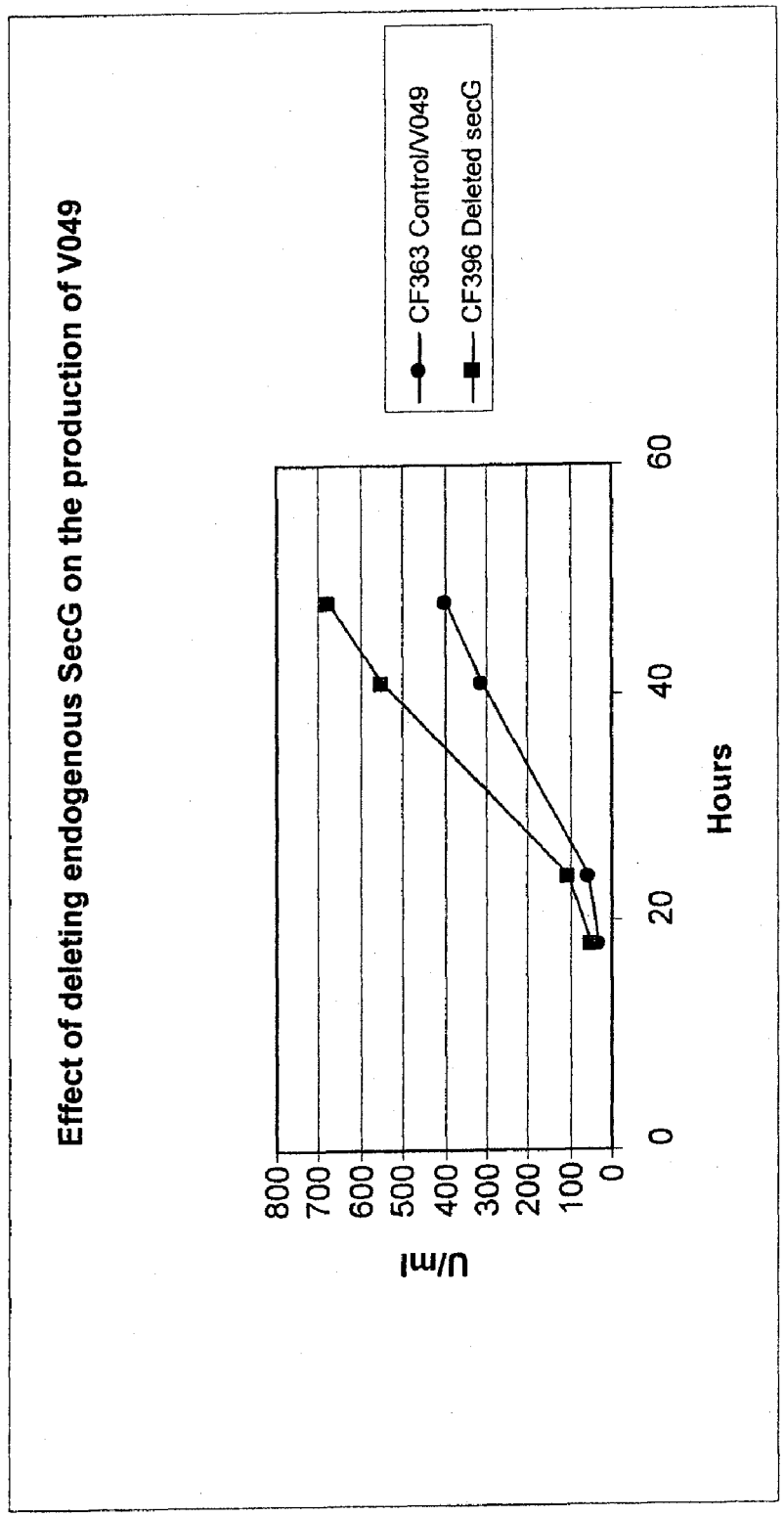
FIG. 9 shows the effect of deleting the endogenous *B. subtilis* secG gene on the production of V049 (CF396) compared to the production of V049 in a *B. subtilis* host (CF363), from which the endogenous secG gene has not been deleted.

As shown in FIG. 9, the secretion of the V049 protease was greater from the *B. subtilis* host cell in which the endogenous secG gene had been deleted (CF396) than from the *B. subtilis* host from which the endogenous secG gene had not been deleted (CF363).

Thus, the production of the heterologous protease V049 in a host strain from which the endogenous secG gene had been removed is greater than that obtained from a host strain in which the native (endogenous) secG gene is not deleted.

EXAMPLE 6

DNA and Amino Acid Sequences of Exemplary Proteases Produced in Host Host Strains DNA Sequence of the truncated *B. clausii* SecG (SEQ ID NO:12)

atgcagctgttttgatgatcgcattaattattgtttctgtcctcttagt cgctgtcgttcttttgcagccaggtcgcagctctgggttatcgggcgcc attactggaggggcagagtagttgctaggaaaacaaaaagcgcgcgggc ttgatgcggtattgcatcgagcaacaatcgtacttgctgttttgtttt tattttgacagggttaaatgcgtatttcctataa The bold, underlined "t" is the mutated base that results in the stop codon at position 40. In the wild type secG it is a "c." Amino Acid Sequence of the Truncated *B. clausii* SecG (SEQ ID NO:11)

MQLFLMIALIIVSVLLVAVVLLQPGRSSGLSGAITGGAE

DNA Sequence of the Full-Length *B. clausii* secG (SEQ ID NO:10)

atgcagctgttttgatgatcgcattaattattgtttctgtcctcttagt cgctgtcgttcttttgcagccaggtcgcagctctgggttatcgggcgc cattactggaggggcagag*c*agttgctaggaaaacaaaaagcgcgcgg gcttgatgcggtattgcatcgagcaacaatcgtacttgctgttttgtttt ttattttgacagggttaaatgcgtatttcctataa Amino Acid Sequence of the Full-Length *B. clausii* SecG (SEQ ID NO:9)

MQLFLMIALIIVSVLLVAVVLLQPGRSSGLSGAITGGAEQLLGKQKARGL
DAVLHRATIVLAVLFFILTGLNAYFL

Amino Acid Sequence of the Full-Length Maxacal Protease (SEQ ID NO:25)

*MKKPLGKIVASTALLISVAFSSSIASA*AEEAKEKYLIGFNEQEAVSEFVE
QVEANDEVAILSEEEEVEIELLHEFETIPVLSVELSPEDVDALELDPAIS
YIEEDAEVTTMAQSVPWGISRVQAPAAHNRGLTGSGVKVAVLDTGISTHP
DLNIRGGASFVPGEPSTQDGNGHGTHVAGTIAALNNSIGVLGVAPNAELY
AVKVLGASGSGSVSSIAQGLEWAGNNGMHVANLSLGSPSPSATLEQAVNS
ATSRGVLVVAASGNSGAGSISYPARYANAMAVGATDQNNNRASFSQYGAG
LDIVAPGVNVQSTYPGSTYASLNGTSMATPHVAGAAALVKQKNPSWSNVQ
IRNHLKNTATSLGSTNLYGSGLVNAEAATR

Amino Acid Sequence of the Full-Length Puramax (V049) Protease (SEQ ID NO:26)

*VRSKKLWIVASTALLISVAFSSSIASA*AEEAKEKYLIGFNEQEAVSEFVE
QVEANDEVAILSEEEEVEIELLHEFETIPVLSVELSPEDVDALELDPAIS
YIEEDAEVTTMAQSVPWGISRVQAPAAHNRGLTGSGVKVAVLDTGISTHP
DLNIRGGASFVPGEPSTQDGNGHGTHVAGTIAALNNSIGVLGVAPNAELY
AVKVLGASGSGSVSSIAQGLEWAGNNVMHVANLSLGLQAPSATLEQAVNS
ATSRGVLVVAASGNSGAGSISYPARYANAMAVGATDQNNNRASFSQYGAG
LDIVAPGVNVQSTYPGSTYASLNGTSMATPHVAGAAALVKQKNPSWSNVQ
IRNHLKNTATSLGSTNLYGSGLVNAEAATR

Amino Acid Sequence of the Full-Length V049-E33Q (SEQ ID NO:27)

*VRSKKLWIVASTALLISVAFSSSIASA*AEEAKQKYLIGFNEQEAVSEFVE
QVEANDEVAILSEEEEVEIELLHEFETIPVLSVELSPEDVDALELDPAIS
YIEEDAEVTTMAQSVPWGISRVQAPAAHNRGLTGSGVKVAVLDTGISTHP
DLNIRGGASFVPGEPSTQDGNGHGTHVAGTIAALNNSIGVLGVAPNAELY
AVKVLGASGSGSVSSIAQGLEWAGNNVMHVANLSLGLQAPSATLEQAVNS
ATSRGVLVVAASGNSGAGSISYPARYANAMAVGATDQNNNRASFSQYGAG
LDIVAPGVNVQSTYPGSTYASLNGTSMATPHVAGAAALVKQKNPSWSNVQ
IRNHLKNTATSLGSTNLYGSGLVNAEAATR

Amino Acid Sequence of the Full-Length V049-E33R (SEQ ID NO:28)

*VRSKKLWIVASTALLISVAFSSSIASA*AEEAKRKYLIGFNEQEAVSEFVE

QVEANDEVAILSEEEEVEIELLHEFETIPVLSVELSPEDVDALELDPAIS

YIEEDAEVTTMAQSVPWGISRVQAPAAHNRGLTGSGVKVAVLDTGISTHP

DLNIRGGASFVPGEPSTQDGNGHGTHVAGTIAALNNSIGVLGVAPNAELY

AVKVLGASGSGSVSSIAQGLEWAGNNVMHVANLSLGLQAPSATLEQAVNS

ATSRGVLVVAASGNSGAGSISYPARYANAMAVGATDQNNNRASFSQYGAG

LDIVAPGVNVQSTYPGSTYASLNGTSMATPHVAGAAALVKQKNPSWSNVQ

IRNHLKNTATSLGSTNLYGSGLVNAEAATR

Amino Acid Sequence of the Properase Protease (SEQ ID NO:29)

*MRSKKLWIVASTALLISVAFSSSIASA*AEEAKEKYLIGFNEQEAVSEFVE

QVEANDEVAILSEEEEVEIELLHEFETIPVLSVELSPEDVDALELDPAIS

YIEEDAEVTTMAQSVPWGISRVQAPAAHNRGLTGSGVKVAVLDTGISTHP

DLNIRGGASFVPGEPSTQDGNGHGTHVAGTIAALNNSIGVLGVAPNAELY

AVKVLGASGGGSNSSIAQGLEWAGNNGMHVANLSLGSPSPSATLEQAVNS

ATSRGVLVVAASGNSGAGSISYPARYANAMAVGATDQNNNRASFSQYGAG

LDIVAPGVNVQSTYPGSTYASLNGTSMATPHVAGAAALVKQKNPSWSNVQ

IRNHLKNTATSLGSTNLYGSGLVNAEAATR

DNA Sequence of the Full-Length Maxacal Protease (SEQ ID NO:30)

*Atgaagaaaccgttggggaaaattgtcgcaagcaccgcactactcatttctgttgcttttagttcatcgatcgcatcggct*gctgaa gaagcaaaagaaaaatatttaattggctttaatgagcaggaagctgtcagtgagtttgtagaacaagtagaggcaaatg acgaggtcgccattctctctgaggaagaggaagtcgaaattgaattgcttcatgaatttgaaacgattcctgttttatccgt tgagttaagcccagaagatgtggacgcgcttgaactcgatccagcgatttcttatattgaagaggatgcagaagtaacg acaatggcgcaatcagtgccatggggaattagccgtgtgcaagcccagctgcccataaccgtggattgacaggttctggtgta aaagttgctgtcctcgatacaggtatttccactcatccagacttaaatattcgtggtggcgctagctttgtaccaggggaaccatcca ctcaagatgggaatgggcatggcacgcatgtggctgggacgattgctgctttaaacaattcgattggcgttcttggcgtagcaccg aacgcggaactatacgctgttaaagtattaggggcgagcggttcaggttcggtcagctcgattgcccaaggattggaatgggca gggaacaatggcatgcacgttgctaatttgagtttaggaagcccttcgccaagtgccacacttgagcaagctgttaatagcgcga cttctagaggcgttcttgttgtagcggcatctgggaattcaggtgcaggctcaatcagctatccggcccgttatgcgaacgcaatgg cagtcggagctactgaccaaaacaacaaccgcgccagcttttcacagtatggcgcagggcttgacattgtcgcaccaggtgtaa acgtgcagagcacatacccaggttcaacgtatgccagcttaaacggtacatcgatggctactcctcatgttgcaggtgcagcagc ccttgttaaacaaaagaacccatcttggtccaatgtacaaatccgcaatcatctaaagaatacggcaacgagcttaggaagcac gaacttgtatggaagcggacttgtcaatgcagaagcggcaacacgctaa DNA Sequence of the Full-Length Puramax (V049) Protease (SEQ ID NO:31)

*gtgagaagcaaaaaattgtggatcgtcgcgtcgaccgcactactcatttctgttgcttttagttcatcgatcgcatcggct*gctgaag aagcaaaagaaaaatatttaattggctttaatgagcaggaagctgtcagtgagtttgtagaacaagtagaggcaaatga cgaggtcgccattctctctgaggaagaggaagtcgaaattgaattgcttcatgaatttgaaacgattcctgttttatccgtt gagttaagcccagaagatgtggacgcgcttgaactcgatccagcgatttcttatattgaagaggatgcagaagtaacg acaatggcgcaatcggtaccatggggaattagccgtgtgcaagcccagctgcccataaccgtggattgacaggttctggtgta aaagttgctgtcctcgatacaggtatttccactcatccagacttaaatattcgtggtggcgctagctttgtaccaggggaaccatcca ctcaagatgggaatgggcatggcacgcatgtggctgggacgattgctgctttaaacaattcgattggcgttcttggcgtagcaccg aacgcggaactatacgctgttaaagtattaggggcgagcggttcaggttcggtcagctcgattgcccaaggattggaatgggca gggaacaatgttatgcacgttgctaatttgagtttaggactgcaggcaccaagtgccacacttgagcaagctgttaatagcgcgac ttctagaggcgttcttgttgtagcggcatctgggaattcaggtgcaggctcaatcagctatccggcccgttatgcgaacgcaatggc agtcggagctactgaccaaaacaacaaccgcgccagcttttcacagtatggcgcagggcttgacattgtcgcaccaggtgtaaa cgtgcagagcacatacccaggttcaacgtatgccagcttaaacggtacatcgatggctactcctcatgttgcaggtgcagcagcc -continued cttgttaaacaaaagaacccatcttggtccaatgtacaaatccgcaatcatctaaagaatacggcaacgagcttaggaagcacg aacttgtatggaagcggacttgtcaatgcagaagcggcaacacgt DNA Sequence of the Full-Length V049-E33Q Protease
(SEQ ID NO:32)

gtgagaagcaaaaaattgtggatcgtcgcgtcgaccgcactactcatttctgttgcttttagttcatcgatcgcatcggctgctgaag aagcaaaacaaaaatatttaattggctttaatgagcaggaagctgtcagtgagtttgtagaacaagtagaggcaaatga cgaggtcgccattctctctgaggaagaggaagtcgaaattgaattgcttcatgaatttgaaacgattcctgttttatccgtt gagttaagcccagaagatgtggacgcgcttgaactcgatccagcgatttcttatattgaagaggatgcagaagtaacg acaatggcgcaatcggtaccatggggaattagccgtgtgcaagcccagctgcccataaccgtggattgacaggttctggtgta aaagttgctgtcctcgatacaggtatttccactcatccagacttaaatattcgtggtggcgctagctttgtaccaggggaaccatcca ctcaagatgggaatgggcatggcacgcatgtggctgggacgattgctgctttaaacaattcgattggcgttcttggcgtagcaccg aacgcggaactatacgctgttaaagtattaggggcgagcggttcaggttcggtcagctcgattgcccaaggattggaatgggca gggaacaatgttatgcacgttgctaatttgagtttaggactgcaggcaccaagtgccacacttgagcaagctgttaatagcgcgac ttctagaggcgttcttgttgtagcggcatctgggaattcaggtgcaggctcaatcagctatccggcccgttatgcgaacgcaatggc agtcggagctactgaccaaaacaacaaccgcgccagcttttcacagtatggcgcagggcttgacattgtcgcaccaggtgtaaa cgtgcagagcacatacccaggttcaacgtatgccagcttaaacggtacatcgatggctactcctcatgttgcaggtgcagcagcc cttgttaaacaaaagaacccatcttggtccaatgtacaaatccgcaatcatctaaagaatacggcaacgagcttaggaagcacg aacttgtatggaagcagacttgtcaatgcagaagcggcaacacgt DNA Sequence of the Full-Length V049-E33R Protease
(SEQ ID NO:33)

gtgagaagcaaaaaattgtggatcgtcgcgtcgaccgcactactcatttctgttgcttttagttcatcgatcgcatcggctgctgaag aagcaaaacgcaaatatttaattggctttaatgagcaggaagctgtcagtgagtttgtagaacaagtagaggcaaatga cgaggtcgccattctctctgaggaagaggaagtcgaaattgaattgcttcatgaatttgaaacgattcctgttttatccgtt gagttaagcccagaagatgtggacgcgcttgaactcgatccagcgatttcttatattgaagaggatgcagaagtaacg acaatggcgcaatcggtaccatggggaattagccgtgtgcaagcccagctacccataaccgtggattgacaggttctggtgta aaagttgctgtcctcgatacaggtatttccactcatccagacttaaatattcgtggtggcgctagctttgtaccaggggaaccatcca ctcaagatgggaatgggcatggcacgcatgtggctgggacgattgctgctttaaacaattcgattggcgttcttggcgtagcaccg aacgcggaactatacgctgttaaagtattaggggcgagcggttcaggttcggtcagctcgattgcccaaggattggaatgggca gggaacaatgttatgcacgttgctaatttgagtttaggactgcaggcaccaagtgccacacttgagcaagctgttaatagcgcgac ttctagaggcgttcttgttgtagcggcatctgggaattcaggtgcaggctcaatcagctatccggcccgttatgcgaacgcaatggc agtcggagctactgaccaaaacaacaaccgcgccagcttttcacagtatggcgcagggcttgacattgtcgcaccaggtgtaaa cgtgcagagcacatacccaggttcaacgtatgccagcttaaacggtacatcgatggctactcctcatgttgcaggtgcagcagcc cttgttaaacaaaagaacccatcttggtccaatgtacaaatccgcaatcatctaaagaatacggcaacgagcttaggaagcacg aacttgtatggaagcggacttgtcaatgcagaagcggcaacacgt DNA Sequence of the Properase Protease (SEQ ID NO:34)

atgaagaaaccgttggggaaaattgtcgcaagcaccgcactactcatttctgttgcttttagttcatcgatcgcatcggctgctgaa gaagcaaaagaaaaatatttaattggctttaatgagcaggaagctgtcagtgagtttgtagaacaagtagaggcaaatg acgaggtcgccattctctctgaggaagaggaagtcgaaattgaattgcttcatgaatttgaaacgattcctgttttatccgt

-continued

```
tgagttaagcccagaagatgtggacgcgcttgaactcgatccagcgatttcttatattgaagaggatgcagaagtaacg acaatggcgcaatcggtaccatggggaattagccgtgtgcaagcccagctgcccataaccgtggattgacaggttctggtgta aaagttgctgtcctcgatacaggtatttccactcatccagacttaaatattcgtggtggcgctagctttgtaccaggggaaccatcca ctcaagatgggaatgggcatggcacgcatgtggctgggacgattgctgctttaaacaattcgattggcgttcttggcgtagcaccg aacgcggaactatacgctgttaaagtattaggggcgagcggtggcggttcgaacagctcgattgcccaaggattggaatgggc agggaacaatggcatgcacgttgctaatttgagtttaggaagcccttcgccaagtgccacacttgagcaagctgttaatagcgcg acttctagaggcgttcttgttgtagcggcatctgggaattcaggtgcaggctcaatcagctatccggcccgttatgcgaacgcaatg gcagtcggagctactgaccaaaacaacaaccgcgccagcttttcacagtatggcgcagggcttgacattgtcgcaccaggtgta aacgtgcagagcacatacccaggttcaacgtatgccagcttaaacggtacatcgatggctactcctcatgttgcaggtgcagcag cccttgttaaacaaaagaacccatcttggtccaatgtacaaatccgcaatcatctaaagaatacggcaacgagcttaggaagca cgaacttgtatggaagcggacttgtcaatgcagaagcggcaacacgctaa
```

For the proteases shown above, the polynucleotide and the corresponding amino acid sequence corresponding to the signal peptide are shown in italics, the pro-region is shown in bold and the sequence of the mature protease is underlined.

DNA Sequence of the Variant Pro Sequence of V049 with E33Q (SEQ ID NO:35)

```
gctgaagaagcaaaacaaaatatttaattggctttaatgagcaggaagc tgtcagtgagtttgtagaacaagtagaggcaaatgacgaggtcgccattc tctctgaggaagaggaagtcgaaattgaattgcttcatgaatttgaaacg attcctgttttatccgttgagttaagcccagaagatgtggacgcgcttga actcgatccagcgatttcttatattgaagaggatgcagaagtaacgacaa tg
```

Amino Acid Sequence of the Variant Pro Sequence of V049 with E33Q (SEQ ID NO:36)

```
AEEAKQKYLIGFNEQEAVSEFVEQVEANDEVAILSEEEEVEIELLHEFET

IPVLSVELSPEDVDALELDPAISYIEEDAEVTTM
```

DNA Sequence of the Variant Pro Sequence of V049-with E33R (SEQ ID NO:37)

```
gctgaagaagcaaaacgcaaatatttaattggctttaatgagcaggaagc tgtcagtgagtttgtagaacaagtagaggcaaatgacgaggtcgccattc tctctgaggaagaggaagtcgaaattgaattgcttcatgaatttgaaacg attcctgttttatccgttgagttaagcccagaagatgtggacgcgcttga actcgatccagcgatttcttatattgaagaggatgcagaagtaacgacaa tg
```

Amino Acid Sequence of the Variant Pro Sequence of V049 with E33R (SEQ ID NO:38)

```
AEEAKRKYLIGFNEQEAVSEFVEQVEANDEVAILSEEEEVEIELLHEFET

IPVLSVELSPEDVDALELDPAISYIEEDAEVTTM
```

All references and publications cited herein are incorporated by reference in their entirety.

It should be noted that there are alternative ways of implementing the present invention. Accordingly, the present embodiments are to be considered as illustrative and not restrictive, and the invention is not to be limited to the details given herein, but may be modified within the scope and equivalents of the appended claims.

---

We claim:

1. An isolated heterologous polynucleotide encoding a heterologous truncated SecG wherein said truncated SecG comprises only one transmembrane region corresponding to the first N-terminal transmembrane segment from a *Bacillus sp*, or a *Geobacillus* wherein said truncated SecG is capable of facilitating the secretion of a desired polypeptide when introduced in a bacterial host cell wherein said bacterial host cell is a *Bacillus* sp.

2. The isolated heterologous polynucleotide of claim 1, wherein the gene encoding for the endogenous SecG of said bacterial host cell is replaced by said heterologous polynucleotide.

3. The isolated heterologous polynucleotide of claim 1, wherein the gene encoding for the endogenous SecG of said bacterial host cell is complemented by said heterologous polynucleotide.

4. The isolated heterologous polynucleotide of claim 1, wherein said truncated SecG is at least 90% identical to the truncated SecG of SEQ ID NO: 11.

5. The isolated heterologous polynucleotide of claim 1, wherein said truncated SecG includes a region of a full-length heterologous SecG.

6. The isolated heterologous polynucleotide of claim 5, wherein said region comprises the first transmembrane domain of said SecG.

7. The isolated heterologous polynucleotide of claim 1, wherein said truncated SecG comprises the first N-terminal 39 amino acids of a SecG chosen from SEQ ID NOS:1-6, 9.

8. An expression vector containing the polynucleotide of claim 1.

9. A polypeptide encoded by the polynucleotide of claim 1.

10. A method for producing a desired polypeptide in a *Bacillus sp* host cell comprising:
(a) expressing a heterologous SecG in said host cell, wherein said heterologous SecG is a truncated SecG comprising only the first N-terminal transmembrane segment from a *Bacillus sp*, or a *Geobacillus* or a sequence with at least 90% identity thereto and (b) producing said desired polypeptide, wherein said heterologous SecG is capable of increasing the amount of said desired polypeptide produced by said host cell as compared to the amount of said desired polypeptide produced by a corresponding host cell that does not express said heterologous SecG.

11. The method of claim 10, wherein said heterologous SecG is encoded by a truncated gene that replaces the endogenous SecG gene of said host cell.

12. The method of claim 10, wherein said heterologous SecG polypeptide is a truncated polypeptide that comprises the first 39 amino acids of the full-length amino acid sequence chosen from SEQ ID NOS: 1-6, 9.

13. A bacterial host cell comprising a *Bacillus sp* where said host cell comprises a polynucleotide fragment encoding only the first N-terminal transmembrane segment of a SecG polypeptide from a *Bacillus sp*, or a *Geobacillus* or a sequence with at least 90% identity thereto and wherein said heterologous SecG is capable of increasing the secretion of a desired polypeptide by said host cell when compared to the secretion of said desired polypeptide by a corresponding host cell that does not express said heterologous SecG.

14. The bacterial host cell of claim 13, wherein said bacterial host cell is a *Bacillus* sp. host cell.

15. The bacterial host cell of claim 13, wherein said bacterial host cell is a *B. subtilis* host cell.

16. The bacterial host cell of claim 13, wherein said desired polypeptide is an enzyme.

17. The bacterial host cell of claim 13, wherein said enzyme is a serine protease.

18. The bacterial host cell of claim 13, wherein said desired polypeptide is chosen from the proteases of SEQ ID NOS: 25-29, 36 and 38, or variant thereof.

19. The bacterial host cell of claim 13, wherein the endogenous SecG gene of said host cell is deleted.

20. The bacterial host cell of claim 13, wherein the endogenous SecG gene of said host cell is complemented by the heterologous SecG gene encoding said heterologous SecG.

21. The bacterial host cell of claim 13, wherein the endogenous SecG gene of said host cell is replaced by a heterologous SecG gene encoding said heterologous SecG.

* * * * *